US008273571B2

(12) United States Patent
Robl et al.

(10) Patent No.: US 8,273,571 B2
(45) Date of Patent: *Sep. 25, 2012

(54) GYNOGENETIC OR ANDROGENETIC PRODUCTION OF PLURIPOTENT CELLS AND CELL LINES, AND USE THEREOF TO PRODUCE DIFFERENTIATED CELLS AND TISSUES

(75) Inventors: James M. Robl, Sioux Falls, SD (US); Jose Cibelli, East Lansing, MI (US); Amy Burnside, Florence, MA (US)

(73) Assignee: Advanced Cell Technology, Inc., Worcester, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/117,184

(22) Filed: May 27, 2011

(65) Prior Publication Data

US 2011/0293580 A1 Dec. 1, 2011

Related U.S. Application Data

(63) Continuation of application No. 10/374,512, filed on Feb. 27, 2003, now Pat. No. 7,951,591, which is a continuation of application No. 09/995,659, filed on Nov. 29, 2001, now abandoned, which is a continuation-in-part of application No. 09/697,297, filed on Oct. 27, 2000, now abandoned.

(60) Provisional application No. 60/161,987, filed on Oct. 28, 1999.

(51) Int. Cl.
*C12N 5/06* (2006.01)
*C12N 5/08* (2006.01)
*C12N 15/88* (2006.01)

(52) U.S. Cl. ........ 435/377; 435/366; 435/373; 435/384; 435/445

(58) Field of Classification Search ................. 435/377, 435/366, 373, 384, 455
See application file for complete search history.

(56) References Cited

U.S. PATENT DOCUMENTS

| 5,464,764 A | 11/1995 | Capecchi et al. |
| 5,496,720 A | 3/1996 | Susko-Parrish et al. |
| 5,827,690 A | 10/1998 | Meade et al. |
| 5,831,141 A | 11/1998 | Lubon et al. |
| 5,843,754 A | 12/1998 | Susko-Parrish et al. |
| 5,843,780 A | 12/1998 | Thomson |
| 6,077,710 A | 6/2000 | Susko-Parrish et al. |
| 6,194,202 B1 | 2/2001 | Susko-Parrish et al. |
| 6,200,806 B1 | 3/2001 | Thomson |
| 6,204,431 B1 | 3/2001 | Prieto et al. |
| 6,255,554 B1 | 7/2001 | Lubon et al. |
| 6,280,718 B1 | 8/2001 | Kaufman et al. |
| 6,680,199 B1 | 1/2004 | Susko-Parrish et al. |
| 7,732,202 B2 | 6/2010 | Revazova et al. |
| 7,951,591 B2 | 5/2011 | Robl et al. |
| 2001/0024825 A1 | 9/2001 | Thomson |
| 2003/0129745 A1 | 7/2003 | Robl et al. |
| 2004/0014206 A1 | 1/2004 | Robl et al. |
| 2008/0075702 A1 | 3/2008 | Robl et al. |
| 2010/0233143 A1 | 9/2010 | Revazova et al. |
| 2010/0248989 A1 | 9/2010 | Revazova et al. |
| 2011/0293580 A1 | 12/2011 | Robl et al. |

FOREIGN PATENT DOCUMENTS

| AU | 782846 | 12/2005 |
| CN | 100497598 | 6/2009 |
| IL | 149175 | 3/2001 |
| IL | 149175 | 3/2011 |
| NZ | 518365 | 8/2004 |
| WO | WO 2007/019398 | 2/2007 |

OTHER PUBLICATIONS

Brevini, et al. (2008) *Stem Cell Rev.* 4: 474-478.
Cri du chat Syndrome, retrieved online at: http://www.naturalstandard.com/monographs/conditions/condition-criduchat.asap. printed Sep. 18, 2009.
Database EMBL [Online] (2001) *Homo sapiens* cDNA FLJ14549 fis, clone NTRM2001670, weakly similar to Zinc Finger Protein 29, XP002589470 retrieved from ESI Accession No. ESI: AK027455 Database Accession No. AK027455.
Database EMBL [Online] (2004) Sequence 759 from Patent WO02068579, XP002589477 retrieved from EBI Accession No. EMBL: CQ714825 Database Accession No. CQ714825.
Database EMBL, [Online] (2006) "SubName: Full=ZSCAN 10 Protein Flags Fragment," XP002589476 retrieved from EBI Accession No. UNIPROT: Q1WWM2 Database Accession No. Q1WWM2.
Database EMBL [Online] (2006) *Homo sapiens* zinc finger and SCAN domain containing 10, mRNA (cDNA clone IMAGE 4000761 0), partial cds, XP002589478 retrieved from EBI Accession No. EMBL: BC1144452 Database Accession No. BC114452.
Database UniProt [Online] (2001) RecName: Full=Zinc Finger and SCAN domain-containing protein 10; AllName: Full=Zinc finger Protein 206, XP002589475 retrieved from EBI Accession No. UNIPROT: Q96SZ4 Database Accession No. Q96SZ4.
Dattena et al., Mol. Reprod. Develop., vol. 73. pp. 31-39, 2006.
Decision of the Opposition Division for the European Patent EP 0 695 351 (EP Appl. No. 94 913 174.2).
Denning et al., Reproduction, vol. 126, pp. 1-11, 2003.
Sturm, et al. (1997) *Development Genes and Evolution*, 206(6): 377-388.
Mann, et al. (1990) *Cell*, 62: 251-260.
Taylor, et al. (1994) *Human Reproduction*, 9(12): 2389-2397.
Kim, et al. (2007) *Cell Stem Cell*, 1(3): 346-352.
Cibelli, et al. (2001) *The Journal of Regenerative Medicine*, 2: 25-31.
Cibelli, et al. (2002) *Scientific American*, 286(1): 43-49.
McCarthy (2001) *The Lancet*, 358: 1877.
Holden, et al. (2004) *Science*, 306(5705): 2174-2176.
Revazova, et al. (2007) *Cloning and Stem Cells*, 9(3): 432-449.
Vrana, et al. (2003) *Proceedings of the National Academy of Sciences of the United States (PNAS)*, 100(Suppl. 1); 11911-11916.
Partial European Search Report for European 10183704.5 mailed Jun. 14, 2011.
Alberts, et al. *Molecular Biology of the Cell* (3rd Ed. 1994) Chapter 2: Meiosis, 1-10.

(Continued)

*Primary Examiner* — Marcia S Noble
(74) *Attorney, Agent, or Firm* — Hunton & Williams LLP

(57) ABSTRACT

Methods for obtaining pluripotent (embryonic stem) cells from parthenogenetic embryos, especially primates, are provided. These cells are useful for producing differentiated cells, tissues and organs, especially human and non-human primate cells, tissues and organs.

8 Claims, 17 Drawing Sheets

OTHER PUBLICATIONS

Alberts, et al. *Molecular Biology of the Cell* (3rd Ed. 1994) Chapter 20: Germ Cells and Fertilization, 1011-1035.
Allen, et al. (1994) *Development* 120: 1473-1482.
The American Heritage Medical Dictionary (2007) ["trophectoderm"].
Bender, et al. (1995) *Roux's Arch Dev Biol* 204: 436-443.
Barton, et al. (1984) *Nature* 311(5984): 374-376.
Brevini, et al. (2008) *Stem Cell Rev*. 4: 127-135.
Brevini, et al. (2009) "Stem Cells from Parthenogenetic Embryos." ATTI della Societa Italiana di Geinocologia e Ostetricia vol. LXXXV [Abstract].
Cao (2009) *Journal of Experimental Zoology Part A: Ecological Genetics and Physiology* 311A(5): 368-376.
Cibelli, et al. (1998) *Nature Biotechnology* 16: 642-646.
Cibelli, et al. (2001) *The Journal of Regenerative Medicine* 2: 25-31.
Cibelli, et al. (2002) *Science* 295(5556): 819.
Cibelli, et al. (2002) *Scientific American* 286(1): 43-49.
Ciccone & Chen (2009) *Epigenetics* 4(4): 216-220.
Collas, et al. (1993) *Molecular Reproduction and Development* 34: 212-223.
Chaper 2: The Embryonic Stem Cell, Stem Cells: Scientific Progress and Future Research Directions, Department of Health and Human Services, Jun. 2001 <http://stemsells.nih.gov/info/scireport/2001report>.
Cri du chat syndrome (downloaded from www.naturalstandard.com/monographs/condidtions/condition-criduchat.asp) (Sep. 18, 2009) pp. 1-5.
Dattena, et al. (2006) *Mol. Reprod. Develop*. 73: 31-39.
Denning, et al. (2003) *Reproduction* 126: 1-11.
*Dictionary of Biological Chemistry* (1998) Kazutomo Imaburi and Tamio Yamakawa, Eds (3$^{rd}$ Ed.) p. 478.
Dinger, et al. (2008) *Stem Cells* 26: 1474-1483.
Frost, et al. (2010) *PLoS Genet*. 6:e1001015.
Genetic Imprinting—Epigenetics 2 from The Australasian Genetics Resource Book (2007), pp. 203-207.
Gjorrett & Maddox-Hyttel (2005) *Reproduction, Fertility and Development* 17(2): 113-124.
Gong, et al. (2009) Human Reproduction 24(4): 805-814.
Green (2007) *Nature Genet* 8: 480-485.
Herzog, et al. (1994) *Development* 120: 1643-1649.
Holden, et al. (2002) *Science* 295(5557): 947.
Holden, et al. (2004) *Science* 306(5705): 2174-2176.
Horri, et al. (2008) Stem Cells 25: 79-88.
Hwang, et al. (2004) *Science* 303: 1669-1674 [RETRACTED Jan. 12, 2006].
Hore, et al. (2007) *Trend Genet* 23(9): 440-448.
Jägerbauer, et al. (1992) *Development* 116: 95-102.
Kaufman, et al. (1983) *J. Embroyol. Exp. Morph*. 73: 249-261.
Keverne (2001) *Prog Brain Res*. 133: 279-285.
Kim, et al. (2007) *Science* 315: 482-486.
Kim, et al. (2007) *Cell Stem Cell* 1(3): 346-352.
Kono, et al. (1993) *Molecular Reproduction and Development* 34: 43-46.
Krivokharchenko, et al. (2003) *Biol Reprod*. 68(3):829-36.
Kure-bayashi, et al. (2000) *Theriogenology* 53(5):1105-19.
Lampert (2008) *Sex Dev* 2: 290-301.
Laguitina, et al. (2004) *Biol. Reprod*. 70(2): 400-405.
Lanza, et al. (2002) *Nature Biotechnology* 20: 117-118.
Lantham & Solter (1991) *Development* 113: 561-568.
Liu, et al. (1998) *Acta zoologica Sinica* 44: 247-248.
Loi, et al. (1998) *Biol Reprod*. 58(5):1177-87.
Langtimm-Sedlak (1996) *Developmental Biology* 174: 345-359.
Mai, et al. (2007) *Cell Research* 17: 1008-1019.
Mann, et al. (1990) *Cell* 62: 251-260.
Marshall, et al. (1998) *Biol Reprod*. Dec. 1998;59(6):1491-7.
McCarthy (2001) *The Lancet* 358: 1877.
Meenambigai & Sejian (2011) *Asian Journal of Animal Sciences* 5(1): 1-18.
Oliveira, et al. (2004) *Human Reproduction* 19(8): 1867-1870.
Newman-Smith, et al. (1995) *Development* 121: 2069-2077.
Niimura (1997) *J. Mamm. Ova Res*. 14: 109-116.
Ozil, et al. (2001) *Development* 128(6):917-28.

Partial European Search Report for European 10183704.5, mailed Jun. 14, 2011.
Purves, Orian, and Heller, Life: The Science of Biology (1995) Chapter 9: Chromosomes and Cell Division pp. 191-213.
Ragina, et al. (2012) *Stem Cells and Development* 21(7): 1134-1144.
Reik, et al. (2001) *Nat Rev Genet*. 2(1):21-32.
Reubinoff, et al. (2000) *Nat. Biotechnol*. 18(4): 399-404.
Revazova, et al. (2007) *Cloning and Stem Cells* 9(3): 432-449.
Saito, et al. (2003) *Biochem. Biophys. Res. Comm*. 309: 104-113.
Santos, et al. (2003) *J Assisted Reprod. Fert*. 20(3): 122-130.
Sasaki, et al. (1992) *Genes Dev*. 6(10): 1843-56.
Schuldiner, et al. (2000) *PNAS* 97(21): 11307-11312.
Senger (1997) Pathways to Pregnancy and Parturition. Current Conceptions, Inc. Pullman, WA pp. 144, 173, and 222.
Shamblott, et al. (1998) *Proc. Natl. Acad. Sci. USA* 95: 13726-31.
Solter (1988) *Annu Rev Genet*. 22:127-46.
Solter, et al. (1975) *Proc. Natl. Acad. Sci USA* 72(12): 5099-102.
Sturm, et al. (1994) *Dev Dyn*. 201(1):11-28.
Strum, et al. (1997) *Development Genes and Evolution* 206(6): 377-388.
Suemori, et al. (2001) *Dev Dyn*. 222(2): 273-279.
Surani, et al. (1983) *Science* 222(4627):1034-6.
Surani, et al. (1984) *Nature* 308(5959): 548-50.
Surani, et al. (1986) *Cell* 45(1): 127-136.
Surani, et al. (1987) *Nature* 326(6111): 395-397.
Surani, et al. (1988) *Development* 103(1): 171-178.
Surani, et al. (1990) *Dev Suppl*. 89-90.
Surani, et al. (1998) *Development* 103(1): 171-178.
Surani, et al. (2007) *C.R. Biologies* 330: 474-478.
Sylvester, et al. (2004) *Arch Surg*. 139: 93-99.
Szabo, et al. (1994) *Development* 120: 1651-1660.
Takagi, et al. (1997) *Mol. Reprod. Develop*., 46: 567-580.
Taylor, et al. (1994) *Human Reproduction* 9(12): 2389-2397.
Thomson, et al. (1998) *Science* 282: 1145-1147.
The American Heritage Medical Dictionary (2007) ["trophectoderm"].
Vrana, et al. (2003) *Proceedings of the National Academy of Sciences of the United States* (PNAS), 100(Suppl. 1): 11911-11916.
Zwanda, et al. (1998) *Nature Medicine* 4: 569-574.
Alberts, et al. *Molecular Biology of the Cell* (3rd Ed.1994) Chapter 2 Meiosis, 1-10.
Alberts, et al. *Molecular Biology of the Cell* (3rd Ed.1994) Chapter 20 Germ Cells and Fertilization, 1011-1035.
Allen et al. (1994) *Development* 120:1473-1482.
Barton et al. Role of paternal and maternal genomes in mouse development, Nature, vol. 311 No. 5984, pp. 374-376, Sep. 27-Oct. 3, 1984.
Bender, et al. (1995) *Arch Dev Biol*. 204: 436-443.
Brandenberger et al. (2004) Nature Biotechnology 22(6): 707-716.
Brevini, et al (2008) *Stem Cell Rev* 4: 127-135.
Brevini, et al. (2009) "Stem Cells from Parthenogenetic Embryos," *ATTI della Società Italiana di Geinocologia e Ostericia* vol. LXXXV [Abstract].
Cao, et al. (Jun. 1, 2009) "Isolation and Culture of Primary Bovine Embryonic Stem Cell Colonies by a Novel Method," *Journal of Experimental Zoology Part A: Ecological Genetics and Physiology* 311A(5): 368-376.
Chapter 2: The Embryonic Stem Cell, Stem Cells: Scientific Progress and Future Research Directions, Department of Health and Human Services, Jun. 2001 <http://stemsells.nih.gov/info/scireport/2001report>.
Cibelli et al., Nature Biotechnology, vol. 16, pp. 642-646, 1998.
Cibelli et al., Parthenogenetic Stem Cells in Nonhuman Primates; www.sciencemag.org; Science, vol. 295, pp. 819, Feb. 1, 2002.
Cibelli et al., The Journal of Regenerative Medicine, vol. 2, pp. 25-31, 2001.
Cibelli, et al. (2002) "Parthenogenetic stem cells in nonhuman primates." *Science* 295(5556): 819.
Collas et al., Molecular Reproduction and Development, vol. 34, pp. 212-223, 1993.
Dinger et al. (2008) Stem Cells 25:1474-1483.
Frost, et al. (2010) "The importance of imprinting in the human placenta." *PLoS Genet*. 6:e1001015.

Gjørret & Maddox-Hyttel (Jan. 1, 2005) "Attempts towards derivation and establishment of bovine embryonic stem cell-like cultures." *Reproduction, Fertility and Development* 17(2): 113-124.
Green, Nature Genet, vol. 8, pp. 480-485, 2007.
Herzog et al., Development, vol. 120, pp. 1643-1649, 1994.
Holden, Science, vol. 295 No. 5556, pp. 779-780, Feb. 2002.
Hore et al., Construction and evolution of imprinted loci in mammals, Trend Genet, vol. 23 No. 9, pp. 440-448, Sep. 23, 2007, Epub Aug. 1, 2007.
Horri, et al. (2009) *Stem Cells* 26: 79-88.
Hwang, et al. (2004) "Evidence of a Pluripotent Human Embryonic Stem Cell Line Derived from a Cloned Blastocyst." *Science* 303: 1669-1674 [RETRACTED Jan. 12, 2006].
Kaufman et al. (1983) Journal of Embryol. Exp. Morph. 73:249-261.
Kim et al. (2007) *Science* 315: 482-486.
Kim, et al. (2007) "Recombination signatures distinguish embryonic stem cells derived by parthenogenesis and somatic cell nuclear transfer." *Cell Stem Cell* 1(3): 346-352.
Kim, et al. (2007) "Recombination signatures distinguish embryonic stem cells deerived by parthenogenesis and somatic cell nuclear transfer." *Cell Stem Cell* 1: 346-352.
Kono et al., Molecular Reproduction and Development, vol. 34, pp. 43-46, 1993.
Krivokharchenko, et al. (2003) "Development of parthenogenetic rat embryos." *Biol Reprod*. 68(3):829-36.
Kure-bayashi, et al. (2000) "Successful implantation of in vitro-matured, electro-activated oocytes in the pig." *Theriogenology* 53(5):1105-19.
Lagutina et al. (2004) Biol. Reprod. 70(2); 400-405.
Lampert Sex Dev. 2:290-301, 2008.
Langtimm-Sedlak, Developmental Biology, vol. 174, pp. 345-359, 1996.
Lanza et al., Nature Biotechnology, vol. 20, pp. 117-118, 2002.
Latham & Solter (1991) "Effect of egg compositon on the development capacity of androgenetic mouse embryos." *Development* 113: 561-568.
Liu et al., Acta Zoologica Sinica, vol. 44, pp. 247-248, 1998.
Loi, et al. (1998) "Development of parthenogenetic and cloned ovine embryos: effect of activation protocols." *Biol Reprod*. 58(5):1177-87.
Mai et al., Cell Research, vol. 17, pp. 1008-1019, 2007.
Mann et al., Androgenetic mouse embryonic stem cells are pluripotent and cause skeletal defects in chimeras: implications for genetic imprinting, Cell, vol. 62 No. 2, pp. 251-260, Jul. 27, 1990.
Mann et al., Cell, vol. 62, pp. 251-260, 1990.
Marshall, et al. (1998) Parthenogenesis activation of marmoset (*Callithrix jacchus*) oocytes and the development of marmoset parthenogenones in vitro and in vivo. Biol Reprod. Dec. 1998;59(6):1491-7.
McCarthy, The Lancet, vol. 358, pp. 1877, 2001.
Newman-Smith et al., Stem cell defects in parthenogetic peri-implantation embryos, Development , vol. 121, pp. 2069-2077, 1995.
Oliveira et al. (2004) *Human Reproduction* 19(8):1867-1870.
Ozil, et al. (2001) "Activation of rabbit oocytes: the impact of the Ca2+ signal regime on development." *Development* 128(6):917-28.
Purves, Orians, and Heller, *Life: The Science of Biology* (1995) Chapter 9 Chromosomes and Cell Division 191-213.
Reik, et al. (2001) "Genomic imprinting: parental influence on the genome." *Nat Rev Genet*. 2(1):21-32.

Reubinoff et al., Embryonic stem cell lines from human blastocysts: somatic differentiation in vitro, Nat. Biotechnol., vol. 18 No. 4, pp. 399-404, Apr. 2000, erratum in: Nat Biotechnol., vol. 18 No. 5, pp. 559, May 2000.
Revazova et al. (2007) *Cloning and Stem Cells*, 9(3): 432-449.
Revozova, et al. (2007) *Cloning and Stem Cells* 9(3): 432-449.
Saito et al., Biochem. Biophys. Res. Comm., vol. 309, pp. 104-113, 2003.
Santos et al., J Assisted Reprod. Fert., vol. 20 No. 3, pp. 122-130, 2003.
Senger (1997) Pathways to Pregnancy and Parturition. Current Conceptions, Inc. Pullman, WA, pp. 144, 173, and 222.
Seumori et al., Establishment of embryonic stem cells lines from cynomolgus monkey blastocysts produced by IVF or ICSI, Dev Dyn. vol. 222 No. 2, pp. 273-279, Oct. 2001.
Shamblott, et al. (1998) "Derivation of pluripotent stem cells from cultured human primordial germ cells." *Proc. Natl. Acad. Sci. USA* 95: 13726-31.
Solter (1988) "Differential imprinting and expression of maternal and paternal genomes," *Annu Rev Genet*, 22:127-46.
Stum et al., Development, Genes and Evolution, vol. 206, pp. 377-388, 1997.
Sturm, et al. (1994) "Abnormal development of embryonic and extraembryonic cell lineages in parthenogenetic mouse embryos." *Dev Dyn*. 201(1):11-28.
Surani (2007) *C.R. Biologies* 330: 474-478.
Surani et al., Influence of chromosomal determinants on development of androgenetic and parthenogenetic cells, Development, vol. 103 No. 1, pp. 171-178, May 1998.
Surani et al., Influence of parental chromosomes on spatial specificity in androgenetic—parthenogentic chimaeras in the mouse, Nature, vol. 326 No. 6111, pp. 395-397, Mar. 26-Apr. 1, 1987.
Surani et al., Nuclear transplantation in the mouse: heritable differences between parental and genomes after activation of the embryonic genome, Cell, vol. 45 No. 1, pp. 127-136, Apr. 11, 1986.
Surani, et al. (1983) "Development of gynogenetic eggs in the mouse: implications for parthenogenetic embryos," *Science* 222(4627):1034-6.
Surani, et al. (May 1988) "Influence of chromosomal determinants on development of androgenetic and parthenogenetic cells," *Development* 103(1); 171-178.
Sylvester et al. (2004) Arch Surg. 139:93-99.
Szabo et al., Development, vol. 120, pp. 1651-1660, 1994.
Szabo et al., Expression and methylation of imprinted genes during in vitro differentiation of mouose parthenogenetic and androgenetic embryonic stem cell lines, Development, vol. 120 No. 6, pp. 1651-1660, Jun. 1994.
Takagi et al., Mol. Reprod. Develop., vol. 146, pp. 567-580, 1997.
Taylor et al., Human Reproduction, vol. 9, pp. 2389-2397, 1994.
Thompson et al. (1998) *Science* 282:1145-1147.
Thomson, et al. (1995) "Isolation of a primate embryonic stem cell line," *Proc. Natl. Acad. Sci USA* 92(17): 7844-7848.
Thomson, et al. (1998) "Embryonic Stem Cell Lines Derived from Human Blastocysts," *Science* 282: 1145-1147.
Vrana et al., Nonhuman primate parthenogenetic stem cell, Proc Natl. Acad. Sci., 100 Suppl. 1, pp. 1911-1916, Sep. 30, 2003, Epub Sep. 22, 2003.
Vrana, et al. (2003) *PNAS* 100(suppl. 1): 11911-11916.
Wang et al. (2007) Journal of Biological Chemistry 282(17): 12822-12830.
Yu et al. (2009) Journal of Biological Chemistry 284(45): 31327-31335.
Zhang et al. (2006) *Nucleic Acids Research* 34(17) 4780-4790.
Zwanda et al., Nature Medicine, vol. 4, pp. 569-574, 1998.

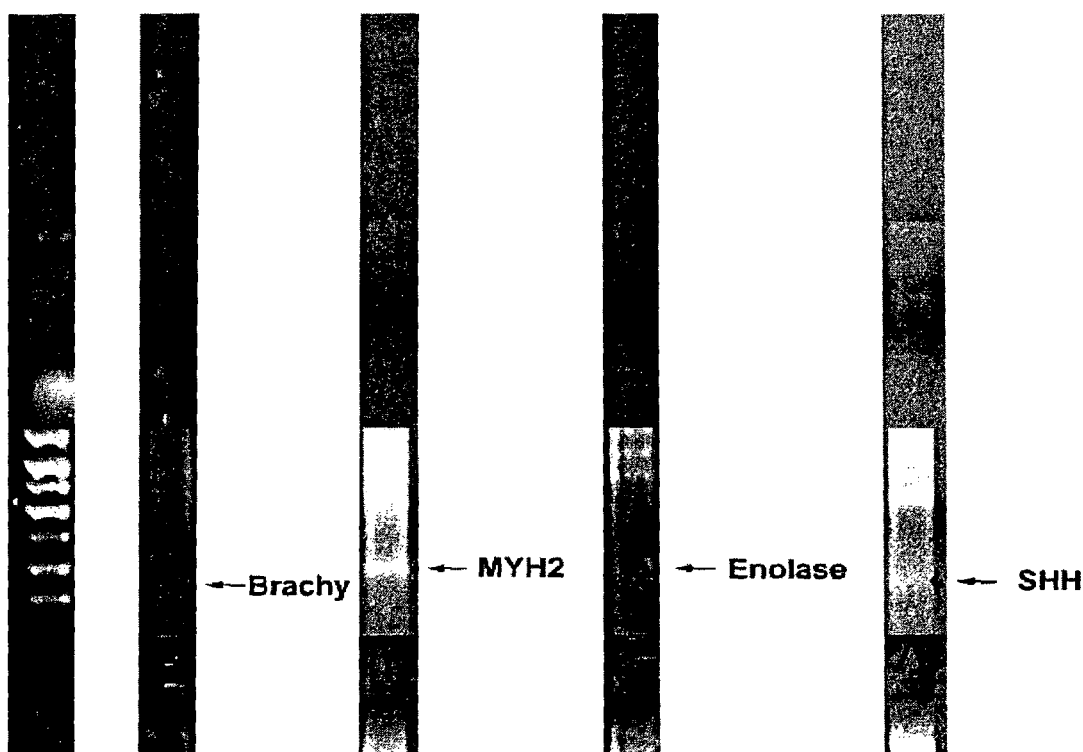
Figure 16. RT-PCR results demonstrating differentiation of multiple somatic cell types in differentiating PPSCs. Brachy: Brachyury (T) protein, MYH2: Skeletal myosin Heavy Polypeptide 2, Enolase: Human neuron-specific Enolase 2, SHH: Human homolog of Sonic Hedgehog.

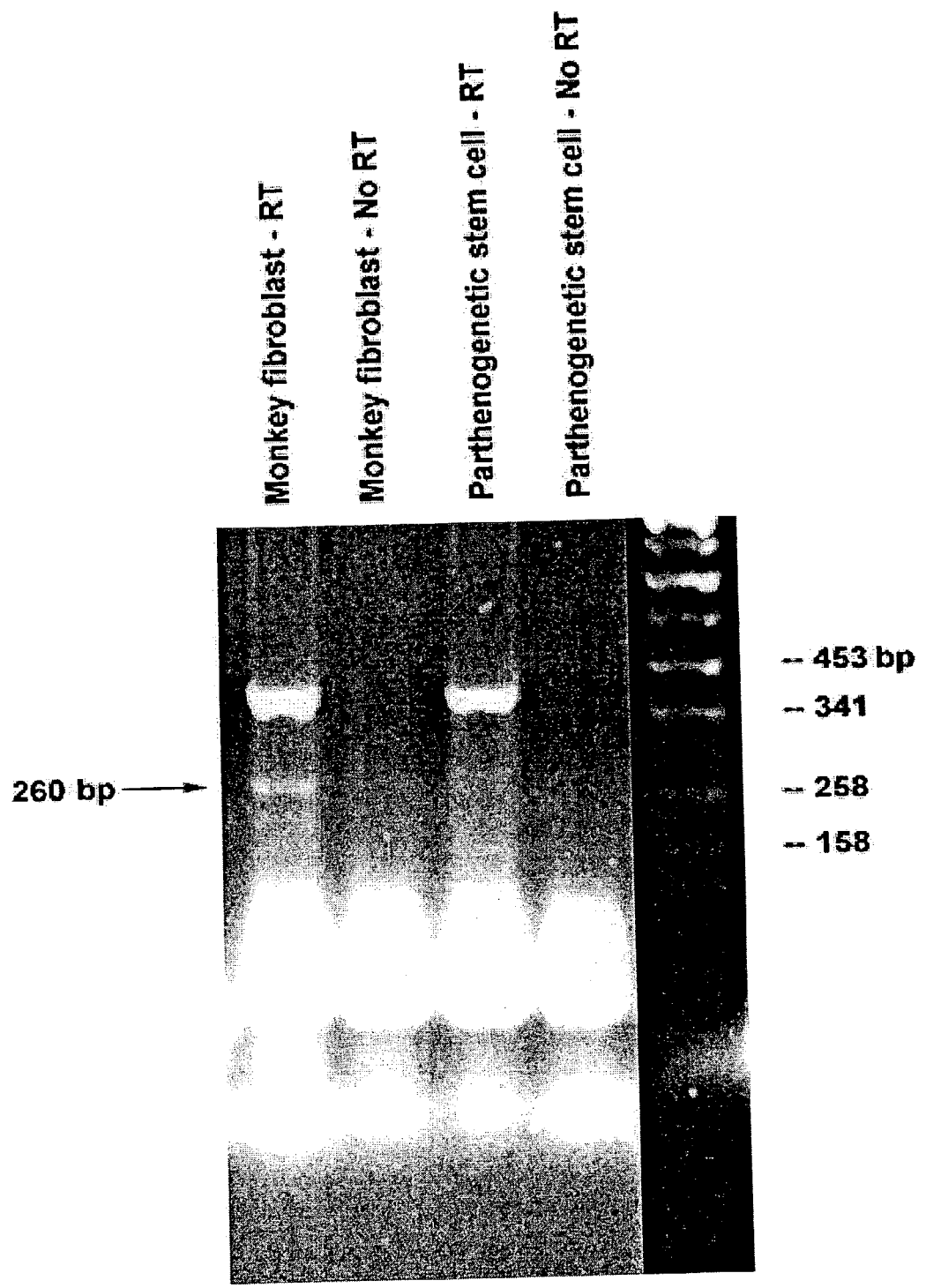
Figure 17. RT-PCR for snrpn in PPSCs.

GYNOGENETIC OR ANDROGENETIC PRODUCTION OF PLURIPOTENT CELLS AND CELL LINES, AND USE THEREOF TO PRODUCE DIFFERENTIATED CELLS AND TISSUES

CROSS REFERENCE TO RELATED APPLICATION

This application is a continuation of U.S. patent application Ser. No. 10/374,512, filed Feb. 27, 2003, now U.S. Pat. No. 7,951,591, which is a continuation of U.S. patent application Ser. No. 09/995,659, filed Nov. 29, 2001 now abandoned, which is a continuation-in-part application of U.S. patent application Ser. No. 09/697,297, filed Oct. 27, 2000 now abandoned, which claims priority from U.S. Provisional Application No. 60/161,987, filed on Oct. 28, 1999, each of which are herein incorporated by reference.

GOVERNMENT RIGHTS

This invention was developed under a federally sponsored research project, i.e., USDA Grant No. 97-35203-4905 and, therefore, the United States Government may have certain rights in the invention.

FIELD OF THE INVENTION

The present invention provides a novel method for producing pluripotent mammalian cell lines and differentiated cells, tissues and organs derived therefrom. Unlike previous reported methods for producing pluripotent cells, the subject pluripotent cells will be produced by gynogenetic or androgenetic means, i.e., methods wherein the pluripotent cells are derived from oocytes containing only DNA of male or female origin and therefore will comprise all female-derived or male-derived DNA. In a preferred embodiment, the oocytes will comprise male or female-derived DNA of primate origin, e.g. human.

BACKGROUND OF THE INVENTION

After ovulation, the oocytes of most mammals remain blocked at the second metaphase stage of meiosis and will eventually degenerate unless sperm penetration takes place. Sperm entry activates a whole series of events in the oocyte which leads to fertilization and the development of a new individual. The earliest changes that can be recognized in the oocyte during activation are the completion of meiosis with the omission of the second polar body and the release of the cortical granules. This is followed by the formation of the male and female pronuclei containing their respective haploid sets of chromosomes. A period of DNA synthesis occurs before the two sets of chromosomes condense and come together on the mitotic spindle of the first cleavage division. Fertilization is completed with the restoration of the diploid complement of chromosomes in the nuclei of the two-cell embryo.

However, it is also known that under certain conditions, which may occur spontaneously in vivo, or in vitro, under controlled conditions, that oocytes containing DNA of all male or female origin may because activated and result in the production of an embryo. Typically such embryo does not develop into an offspring, but rather stops developing fairly early in embryogenesis.

The activation of oocytes and development of embryos that comprise DNA of all male or female origin is typically effected as a means of studying embryogenesis. For example, the activation of oocytes containing DNA of all female origin, without any contribution from the male gamete, and the production of an embryo therefrom, is known as "parthenogenesis." This method has been used by many researchers as a means for studying embryogenesis in vitro.

Parthenogenesis is a type of gynogenesis. Gynogenesis broadly is defined as the phenomena wherein an oocyte containing all female DNA becomes activated and produces an embryo. Gynogenesis includes parthenogenesis as well as activation methods wherein the spermatozoa activates the oocyte to complete meiosis, but fails to contribute any genetic material to the resulting embryo. As in parthenogenesis, the activated oocyte does not contain DNA of male origin. However, unlike parthenogenesis, however, the male gamete does make a contribution, i.e., it stimulates oocyte activation.

Androgenesis can be considered to be the opposite of gynogenesis. This refers to the production and activation of an oocyte containing DNA of entirely male origin, and the development of an embryo therefrom.

In general, embryos that result from oocytes containing DNA of all female or male origin only develop to a certain point, and then stop developing. This is hypothesized to occur, e.g., in the case of parthenogenetic embryos of the instability of the aging unfertilized oocyte in the maintenance of the meiotic block. In fact, parthenogenetically activated oocytes may give rise to a variety of aberrations that occur during the completion of meiosis, which may result in the production of embryos of different genetic constitutions.

It is known that artificial activation of mammalian oocytes, including oocytes containing DNA of all male or female origin, can be induced by a wide variety of physical and chemical stimuli. Examples of such methods are listed in the Table below.

TABLE 1

List of physical and chemical stimuli which can induce oocyte activation in mammals.

| Physical | Chemical |
|---|---|
| Mechanical pricking | Enzymatic trypsin, pronase, hyaluilanidase |
| manipulation of oocytes in vitro | Osmotic |
| Thermal | Ionic |
| cooling | divalent cations |
| heating | calcium ionophores |
| Electric | Anaesthetics |
| | general - ether, ethanol, nembutal, chloroform, avertin |
| | local - dibucaine, tetracaine, lignocaine, procaine |
| | Phenothiazine, tranquilizers thioridazine, trifluoperazine, fluphenazine, chlorpromazine |
| | Protein synthesis inhibitors cycloheximide, puromycin |
| | Phosphorylation inhibitors (e.g., DMAP) |
| | Inisitol 1,4,5-triphosphate (Ins P3) |

Indeed, the activation of parthenogenetic oocytes has been well reported in the literature. For example, Ware et al, *Gamete Research*, 22:265-275 (1989) teach the ability of bovine oocytes to undergo parthenogenetic activation using $Ca^{++}$, $Mg^{++}$—$H^+$ ionophore (A23187) or electric shock. Also, Yang et al, *Soc. Study Reprod.*, 46:117 (1992) teaches activation of bovine follicular oocytes using cycloheximide and electric pulse treatment. Graham C. F. in *Biol. Rev.*, 49:399-422 (1979) describes then existing methods for activating parthenogenetic mammalian embryos. Further, Matthew H. Kaufman, in *Prog. in Anat*, Vol. 1:1-34, ed. R. G. Harrison and R. L. Holmes, Cambridge Press, London, UK (1981) reviews parthenogenesis and methods of activation. The parthenogenetic activation of rabbit and mouse oocytes is also disclosed by Ozil, Jean Pierre, *Devel.*, 109:117-127 (1990); Kubiak, Jacek, *Devel. Biol.*, 136:537-545 (1989); Onodera et al, *Gamete Research*, 22:277-283 (1989); Siracusa et al, *J. Embryol. Exp. Morphol.*, 43:157-166 (1978); and Szollosi et al, *Chromosoma*, 100:339-354 (1991). Still further, the activation of unfertilized sea urchin eggs is disclosed by Steinhardt et al, *Nature*, 252:41-43 (1974); and Whitaker, M., *Nature*, 342:636-639 (1984). Also, the parthenogenetic activation of human oocytes has been reported. (See, e.g., De Sutter et al, *J. Associated Reprod. Genet.*, 9(4):328-336 (1992).)

In general, the goal of such artificial oocyte activation methods has been known in biological research, in particular the study of embryonic development, and the mechanisms which are involved in oocyte activation.

In recent years, a significant goal of many research groups has been the identification of methods that efficiently and reproducibly give rise to pluripotent or embryonic stem cells (ES cells), and ES or pluripotent cell lines. ES cells are extremely desirable because of their pluripotency which allows them to give rise to any differentiated cell type. Also, ES cells are useful for the production of chimeric animals and as an in vitro model for differentiation studies, especially the study of genes involved in early development.

Methods for deriving embryonic stem (ES) cell lines in vitro from early preimplantation mouse embryos are well known. (See, e.g., Evans et al., *Nature*, 29:154-156 (1981); Martin, *Proc. Natl. Acad. Sci., USA*, 78:7634-7638 (1981)). ES cells can be passaged in an undifferentiated state, provided that a feeder layer of fibroblast cells (Evans et al., Id.) or a differentiation inhibiting source (Smith et al., *Dev. Biol.*, 121: 1-9 (1987)) is present.

ES cells have been previously reported to possess numerous applications. For example, it has been reported that ES cells can be used as an in vitro model for differentiation, especially for the study of genes which are involved in the regulation of early development. Mouse ES cells can give rise to germline chimeras when introduced into preimplantation mouse embryos, thus demonstrating their pluripotency (Bradley et al., *Nature*, 309:255-256 (1984)).

In view of their ability to transfer their genome to the next generation, ES cells have potential utility for germline manipulation of livestock animals by using ES cells with or without a desired genetic modification. Moreover, in the case of livestock animals, e.g., ungulates, nuclei from like preimplantation livestock embryos support the development of enucleated oocytes to term (Smith et al., *Biol. Reprod*, 40:1027-1035 (1989); and Keefer et al., *Biol. Reprod.*, 50:935-939 (1994)). This is in contrast to nuclei from mouse embryos which beyond the eight-cell stage after transfer reportedly do not support the development of enucleated oocytes (Cheong et al, *Biol. Reprod.*, 48:958 (1993)). Therefore, ES cells from livestock animals are highly desirable because they may provide a potential source of totipotent donor nuclei, genetically manipulated or otherwise, for nuclear transfer procedures.

Some research groups have reported the isolation of purportedly pluripotent embryonic cell lines. For example, Notarianni et al., *J. Reprod. Fert. Suppl.*, 43:255260 (1991), reports the establishment of purportedly stable, pluripotent cell lines from pig and sheep blastocysts which exhibit some morphological and growth characteristics similar to that of cells in primary cultures of inner cell masses isolated immunosurgically from sheep blastocysts. Also, Notarianni et al., *J. Reprod. Fert. Suppl.*, 41:51-56 (1990) discloses maintenance and differentiation in culture of putative pluripotential embryonic cell lines from pig blastocysts. Gerfen et al., *Anim. Biotech*, 6(1):1-14 (1995) discloses the isolation of embryonic cell lines from porcine blastocysts. These cells are stably maintained in mouse embryonic fibroblast feeder layers without the use of conditioned medium, and reportedly differentiate into several different cell types during culture.

Further, Saito et al., *Roux's Arch. Dev. Biol.*, 201:134-141 (1992) reports cultured, bovine embryonic stem cell-like cell lines which survived three passages, but were lost after the fourth passage. Handyside et al., *Roux's Arch. Dev. Biol.*, 196:185-190 (1987) discloses culturing of immunosurgically isolated inner cell masses of sheep embryos under conditions which allow for the isolation of mouse ES cell lines derived from mouse ICMs. Handyside et al. reports that under such conditions, the sheep ICMs attach, spread, and develop areas of both ES cell-like and endoderm-like cells, but that after prolonged culture only endoderm-like cells are evident.

Cherny et al., *Theriogenology*, 41:175 (1994) reported purportedly pluripotent bovine primordial germ cell-derived cell lines maintained in long-term culture. These cells, after approximately seven days in culture, produced ES-like colonies which stained positive for alkaline phosphatase (AP), exhibited the ability to form embryoid bodies, and spontaneously differentiated into at least two different cell types. These cells also reportedly expressed mRNA for the transcription factors OCT4, OCT6 and HES 1, a pattern of homeobox genes which is believed to be expressed by ES cells exclusively.

Campbell et al., *Nature*, 380:64-68 (1996) reported the production of live lambs following nuclear transfer of cultured embryonic disc (ED) cells from day nine ovine embryos cultured under conditions which promote the isolation of ES cell lines in the mouse. The authors concluded that ED cells from day nine ovine embryos are totipotent by nuclear transfer and that totipotency is maintained in culture.

Van Stekelenburg-Hamers et al., *Mol. Reprod. Dev.*, 40:444-454 (1995), reported the isolation and characterization of purportedly permanent cell lines from inner cell mass cells of bovine blastocysts. The authors isolated and cultured ICMs from 8 or 9 day bovine blastocysts under different conditions to determine which feeder cells and culture media are most efficient in supporting the attachment and outgrowth of bovine ICM cells. They concluded that the attachment and outgrowth of cultured ICM cells is enhanced by the use of STO (mouse fibroblast) feeder cells (instead of bovine uterus epithelial cells) and by the use of charcoal-stripped serum (rather than normal serum) to supplement the culture medium. Van Stekelenburg et al reported, however, that their cell lines resembled epithelial cells more than pluripotent ICM cells.

Smith et al., WO 94/24274, published Oct. 27, 1994, Evans et al, WO 90/03432, published Apr. 5, 1990, and Wheeler et al, WO 94/26889, published Nov. 24, 1994, report the isolation, selection and propagation of animal stem cells which purportedly may be used to obtain transgenic animals. Evans et al. also reported the derivation of purportedly pluripotent embryonic stem cells from porcine and bovine species which assertedly are useful for the production of transgenic animals. Further, Wheeler et al, WO 94/26884, published Nov. 24, 1994, disclosed purported embryonic stem cells which are assertedly useful for the manufacture of chimeric and transgenic ungulates. However, to the best of the inventors' knowledge, this work has never been reported in any peer-reviewed journal.

Quite recently, two research groups simultaneously reported the production of purified non-human primate and human ES cells. These ES cell lines were derived from non-human primate and human embryos. These purported ES cell lines were reported to be SSEA-1 negative, SSEA-4, and SEA-3 positive, TRA-1-60 and TR-A1-81 positive, and alkaline phosphatase positive, to develop into all three embryonic germ layers (endoderm, mesoderm, ectoderm), to maintain a normal karyotype even after prolonged culturing, and to proliferate indefinitely in vitro in an undifferentiated state.

Also recently, a group of scientists at the University of Massachusetts and Advanced Cell Technology reported the production of a "human embryo" by cross species nuclear transplantation of human differentiated cells into a bovine oocyte, and the potential use thereof for the production of human ES cells. However, notwithstanding what has been reported, improved methods for obtaining ES cells, and methods for maintaining such cells in vitro for indefinite periods would be extremely useful.

OBJECTS OF THE INVENTION

Therefore, it is an object of the invention to provide a novel method for producing pluripotent cells and cell lines, i.e., ES cells.

More specifically, it is an object of the invention to provide a method for obtaining pluripotent cells or cell lines that comprise female-derived or male-derived DNA.

Still more specifically, it is an object of the invention to provide a method for obtaining pluripotent cells or cell lines that comprise primate female-derived or male-derived DNA, male or female DNA of human origin.

Related thereto, it is an object of the invention to provide pluripotent cells or cell lines that are isogenic to male or female donors, e.g., a human donor.

Also, it is an object of the invention to utilize pluripotent cells that comprise all female-derived or male-derived DNA for the production of differentiated cells, tissues and organs.

It is a related object of the invention to use pluripotent cells or cell lines, preferably human pluripotent cells or cell lines, to produce primate, preferably human, differentiated cells, tissues or organs by inducing differentiation of pluripotent cells or cell lines that comprise DNA of all mate or female origin.

Further, it is an object of the invention to utilize pluripotent cells that comprise all female-derived or male-derived DNA for the production of chimeric animals.

It is an even more specific object of the invention to produce pluripotent cells containing all male-derived or female-derived DNA by the following method:
(i) producing a cell preferably in metaphase II, preferably an oocyte or blastomere that comprises all male- or female-derived DNA;
(ii) activating such oocyte or blastomere under conditions that (1) does not result in second polar body extrusion or (2) inhibits polar body extrusion, or (3) inhibits the first cleavage event; thereby producing an activated oocyte having a diploid content of DNA of male or female origin;
(iii) culturing the resultant activated oocyte or blastomere under conditions that give rise to an embryo comprising a trophectoderm and inner cell mass; and
(iv) culturing cells derived from said inner cell mass in vitro under conditions that maintain said cells in an undifferentiated, pluripotent state.

It is another more specific object of the invention to produce pluripotent cells containing all male-derived or female-derived DNA by the following method:
(i) transplanting an enucleated oocyte or blastomere with two haploid nuclei, both of either male or female origin;
(ii) activating said oocyte or blastomere;
(iii) culturing said activated oocyte or blastomere under conditions that result in an embryo comprising a trophectoderm and inner cell mass; and
(iv) culturing cells obtained from said inner cell mass in vitro under conditions that maintain said cells in an undifferentiated, pluripotent state.

It is another object of the invention to (I) produce embryos containing DNA of all male or female origin by any of the above-identified methods which contains a discernible inner cell mass and trophectoderm, (ii) selecting cells from said inner cell mass or cells which have been isolated from said inner cell mass and cultured under conditions that maintain said cells in an undifferentiated, pluripotent state; and (iii) to confirm the pluripotency of such selected cells.

This can be effected by various methods, e.g., by testing for the presence of certain molecular markers that are characteristic of pluripotency; by making chimeric animals using said cells and testing for the genetic contribution of said cells to the different cells of the chimeric animal by injection into SCID mice and observing the production of different differentiated cell types, and by observing the differentiation of such cells into embryoid bodies and other types of differentiated cells in tissue culture.

It is another object of the invention to provide a theoretically infinite supply of isogenic pluripotent cells by: (I) producing an embryo derived from all male or female DNA that contains a discernible trophectoderm and inner cell mass; (ii) culturing at least the inner cell mass of said embryo or a portion thereof under conditions that maintain said cells in a pluripotent undifferentiated state. This is preferably effected by culturing the inner cell mass or a portion thereof under conditions whereby such cells or inner cell mass is maintained in contact with a feeder layer, e.g., fetal fibroblasts. These cultured pluripotent cells will be transferred to new feeder layers as often as is required to maintain said cells in the desired pluripotent state.

Another object of the invention is to produce pluripotent cells that comprise a desired DNA modification. This will be effected by producing oocytes containing DNA of all male or female origin, wherein said DNA comprises a desired modification; activating said oocytes under conditions that give rise to an embryo having a discernible trophectoderm and inner cell mass; and culturing cells from said inner cell mass or the entire cell mass under conditions that inhibit differentiation and maintain said cells in a pluripotent state that contain the desired DNA modification.

Still another object of the invention is to produce differentiated cells or tissues that contain a desired DNA modification comprising:
(i) producing oocytes that contain DNA of all male or female origin, which DNA comprises at least one modification;
(ii) activating said oocytes under conditions that give rise to an embryo containing a discernible trophectoderm and inner cell mass;
(iii) culturing at least said inner cell mass or a portion thereof under conditions that maintain said cells in an undifferentiated, pluripotent state; and
(iv) using said cultured cells to produce differentiated cells containing said at least one DNA modification.

This can be effected, e.g., by altering the cell culture procedure, e.g., by addition of growth factors that promote differentiation; by removal of feeder layers, by injection into a suitable animal, e.g., SCID mouse, whereby differentiated cells and/or tissues arise from said cells in vivo; or by the use thereof to produce a chimeric animal or fetus that contains differentiated cells that express the genotype of said male or female DNA, which comprises at least one DNA modification.

Still another object of the invention is to provide cell cultures comprising pluripotent cells which optionally may be genetically modified, wherein said pluripotent cells are derived from embryos produced by androgenetic or gynogenetic methods.

Yet another object of the invention is to provide differentiated cells and tissues derived from pluripotent cells which are themselves derived from embryos produced by androgenetic or gynogenetic methods.

Still another object of the invention is to use said pluripotent cells, or differentiated cells derived therefrom, which optionally may be genetically modified for cell and gene therapy, tissue and organ transplantation, or for the study of embryogenesis and differentiation. For example, the effect of specific DNA modifications on embryonic development or the production of specific types of differentiated cells can be effected.

Yet another object of the invention is to culture pluripotent cells and cell lines produced according to the invention with different combinations of hormones, cytokines, and growth factors and ratios thereof that induce the differentiation of the subject pluripotent cells into particular differentiated cell types.

It is yet another object of the invention to provide cloned animals, having a particular genotype, by use of pluripotent cells, or differentiated cells provided therefrom, produced according to the invention as nuclear donors for nuclear transfer.

It is still another object of the invention to utilize sperm or oocytes from animals having desired characteristics, e.g. preferred agricultural characteristics, for the production of pluripotent cells and cell lines. These pluripotent cells or differentiated cells may be utilized as nuclear transfer donors.

It is another object of the invention to provide a novel business method for producing cloned agricultural animals having a desired genotype by sperm or oocytes derived therefrom for use in the production of pluripotent cells or cell lines having the same genotype.

In a preferred object of the invention, the pluripotent cells or differentiated cells derived therefrom will be obtained by activation of an oocyte that contains only DNA of human male or human female origin, which DNA is optionally genetically modified to produce an embryo containing a discernible trophectoderm and inner cells mass, and wherein the inner cell mass or a portion thereof is cultured under conditions that maintain said cells in a pluripotent undifferentiated state; and which pluripotent cells give rise to differentiated cell types in vivo (e.g., in a SCID mouse), or when cultured under appropriate conditions.

BRIEF DESCRIPTION OF THE DRAWINGS

FIG. 16 shows RT-PCR results demonstrating differentiation of multiple somatic cell types in differentiating PPSCs: Brachy: Brachyury (T) protein, MYH2: Skeletal myosin Heavy Polypeptide 2, Enolase: Human neuron-specific Enolase 2, SHH: Human homolog of Sonic Hedgehog.

FIG. 17 shows RT-PCR results using mRNA from monkey fibroblasts with or without reverse transcriptase and PPSCs with or without reverse transcriptase. A PCR product was detected of the predicted length only in the monkey fibroblasts cells.

DETAILED DESCRIPTION OF THE INVENTION

Figure 1:
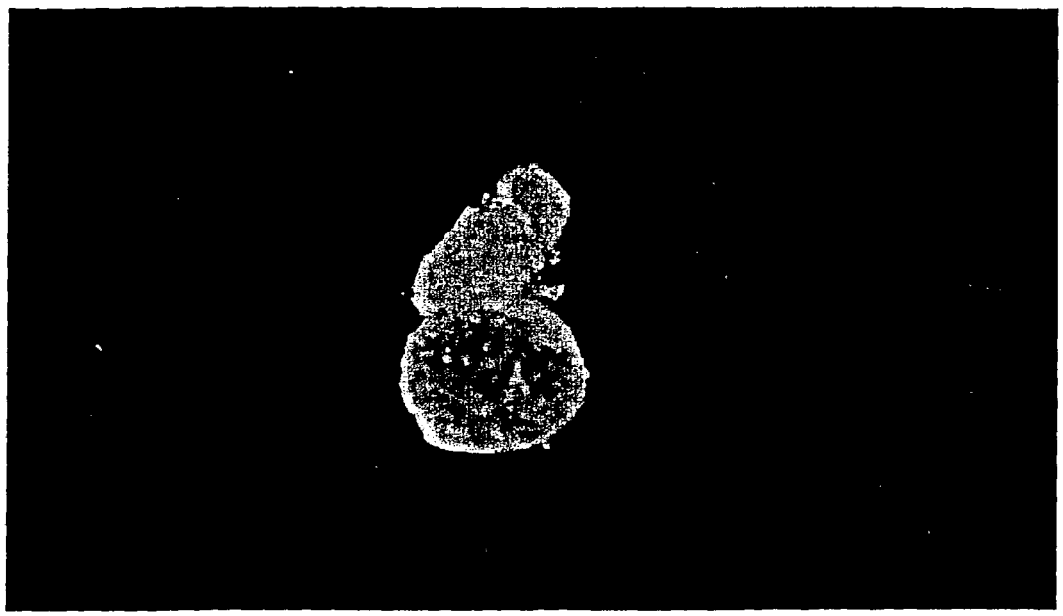
FIG. 1 (labeled 31-11): Embryoid body photographed at 100× magnification. Formed from explant plated directly on culture dish (no mouse fetal fibroblast feeder layer). Original colony (1023981-3) plated from a blastocyst activated previously. Light is deflected showing lipid content of cells.
Figure 2:
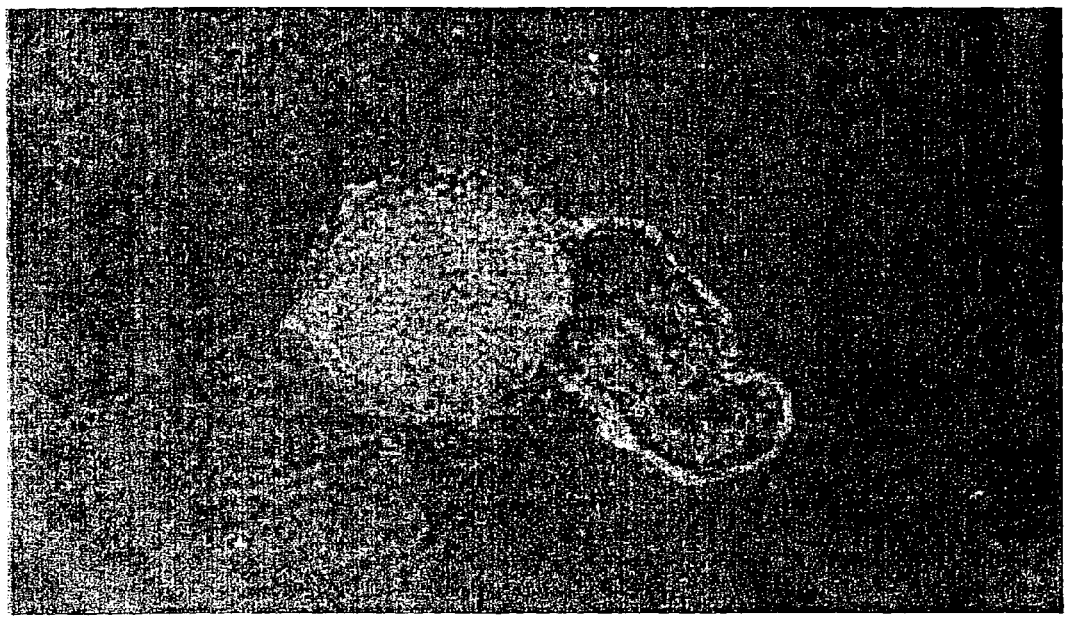
FIG. 2 (labeled 31-18): Embryoid body photographed at 100× magnification. Formed from explant plated directly on culture dish (no mouse fetal fibroblast feeder layer). Original colony (1023981-3) plated from a blastocyst activated a week prior.
Figure 3:
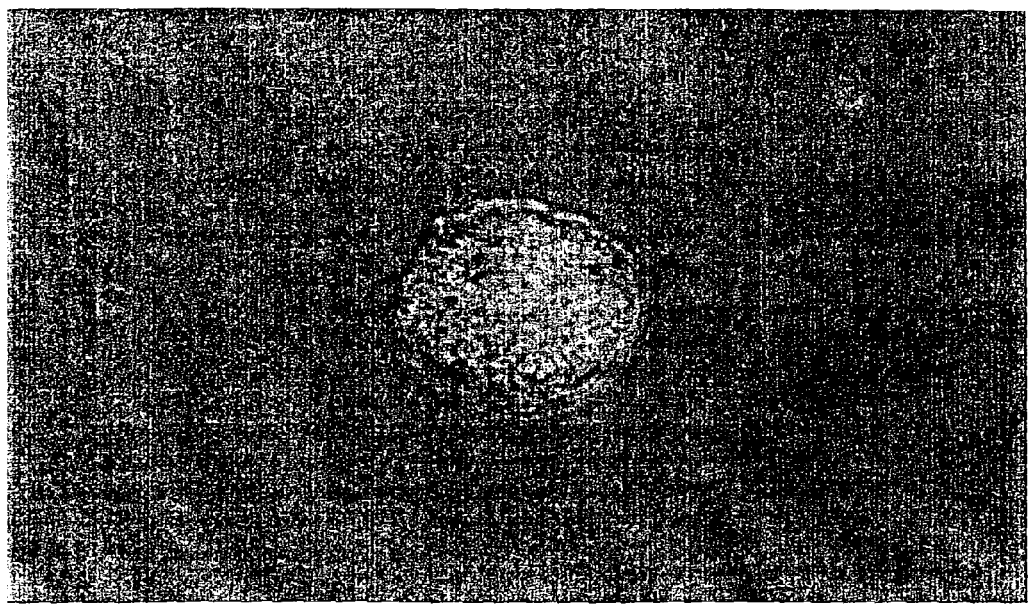
FIG. 3 (labeled 31-25): Embryoid body photographed at 100× magnification. Formed from explant plated directly on culture dish (no mouse fetal fibroblast feeder layer). Original colony (1023981-3) plated from a blastocyst activated week prior.
Figure 4:
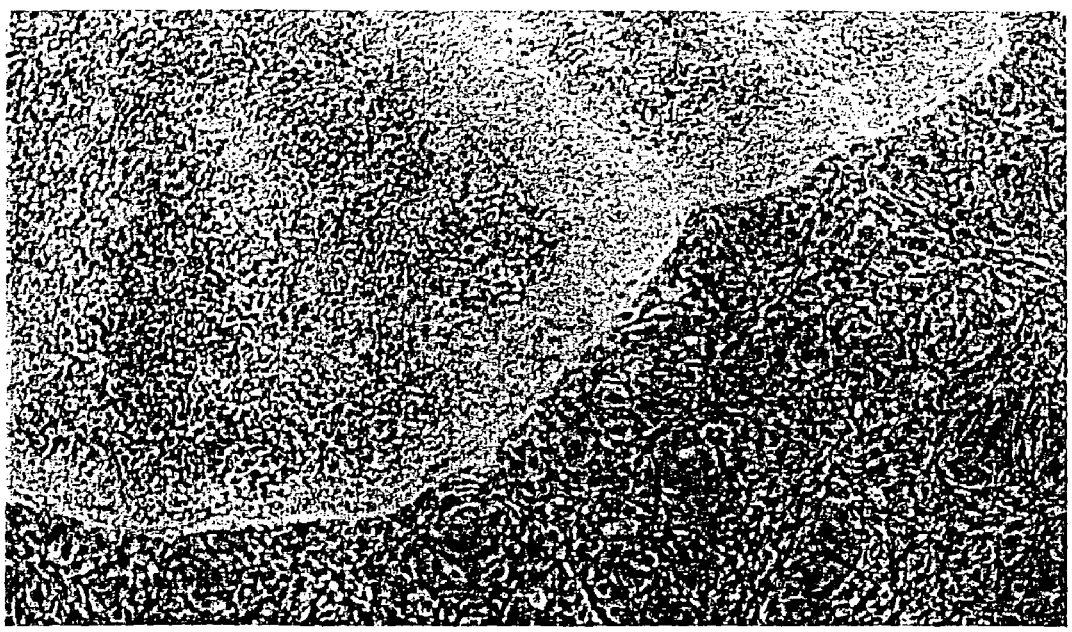
FIG. 4 (labeled 32-1): Edge of explanted stem cell colony photographed at 40× magnification. Original colony (1023981-3) plated from blastocyst activated week prior. Stem cell colony is top left and mouse fetal fibroblast feeder layer is bottom right.
Figure 5:
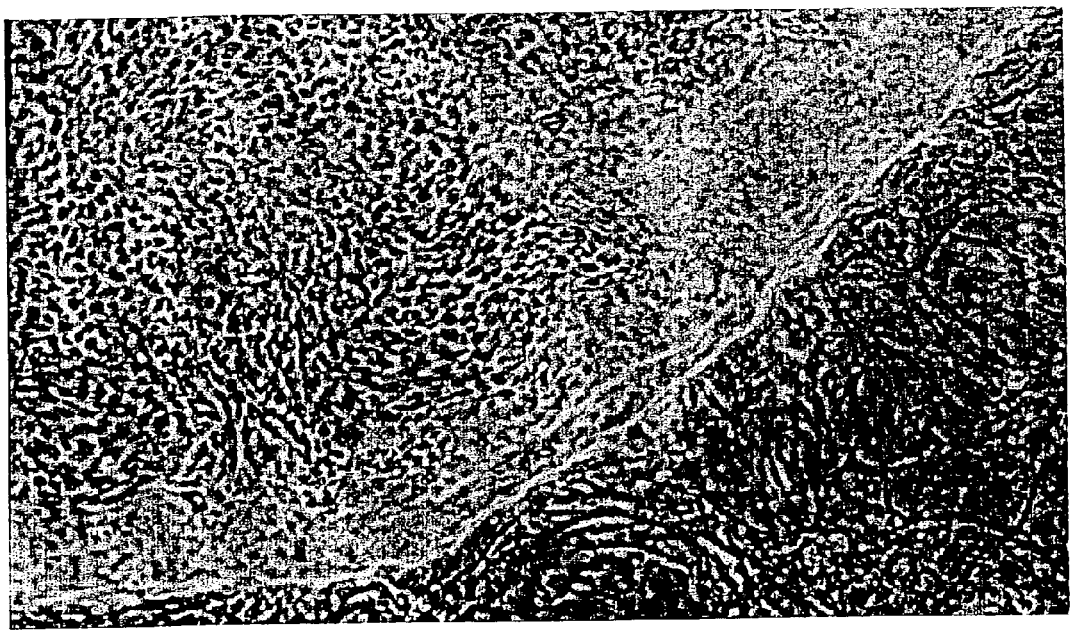
FIG. 5 (labeled 32-3): Edge of explanted stem cell colony photographed at 100× magnification. Original colony (1023981-3) plated from blastocyst activated week prior. Stem cell colony is top left and mouse fetal fibroblast feeder layer is bottom right.
Figure 6:
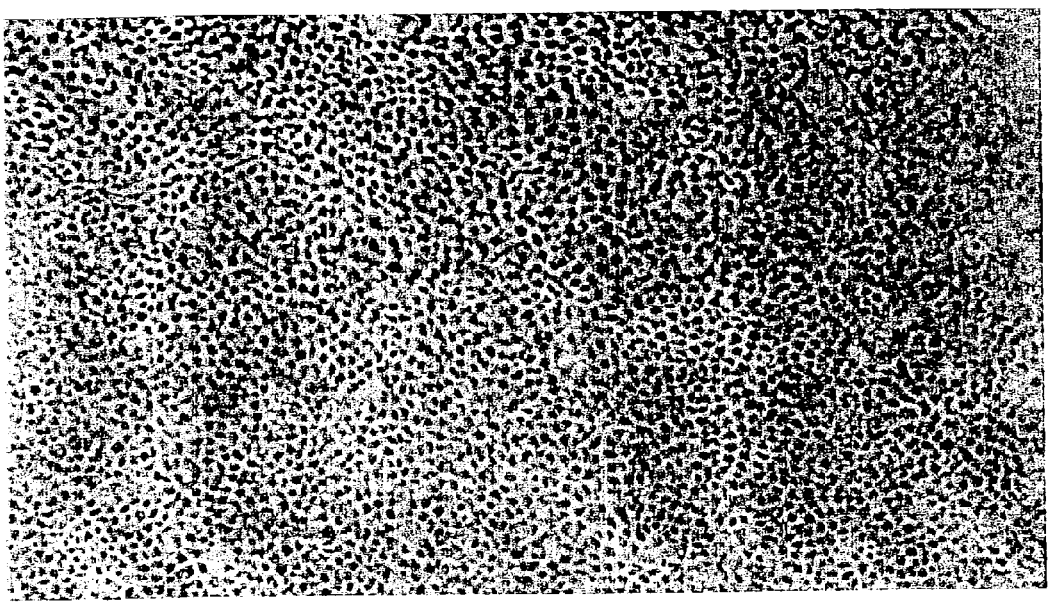
FIG. 6 (labeled 32-5): Center of explanted stem cell colony photographed at 100× magnification. Original colony plated (1023981-3) from blastocyst activated week prior.
Figure 7:
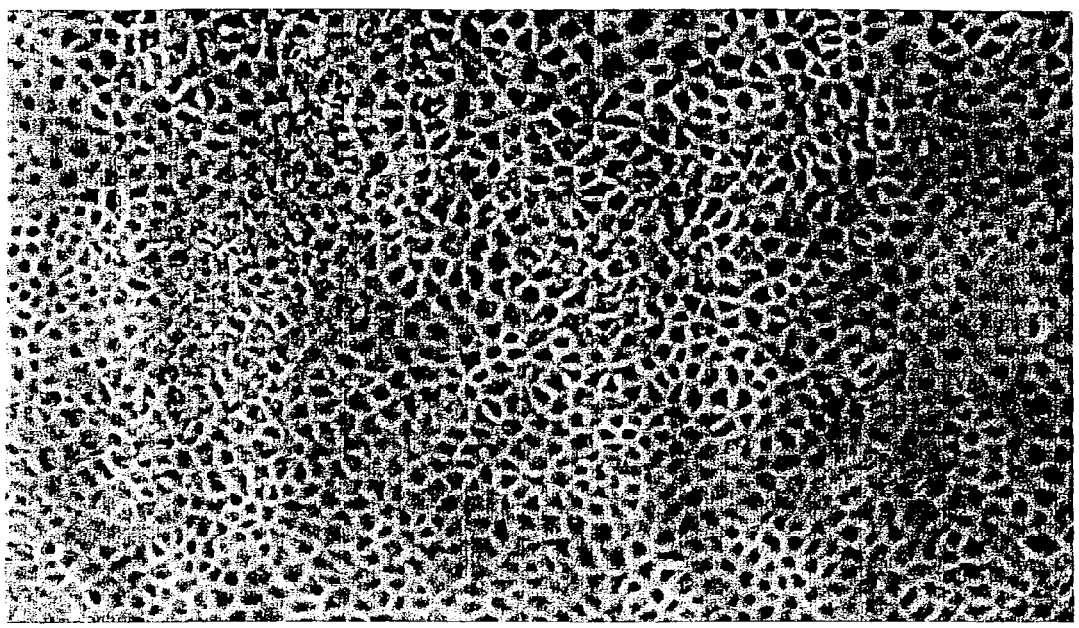
FIG. 7 (labeled 32-12): Center of explanted stem cell colony photographed at 200× magnification. Original colony plated (1023981-3) from blastocyst activated week prior.
Figure 8:
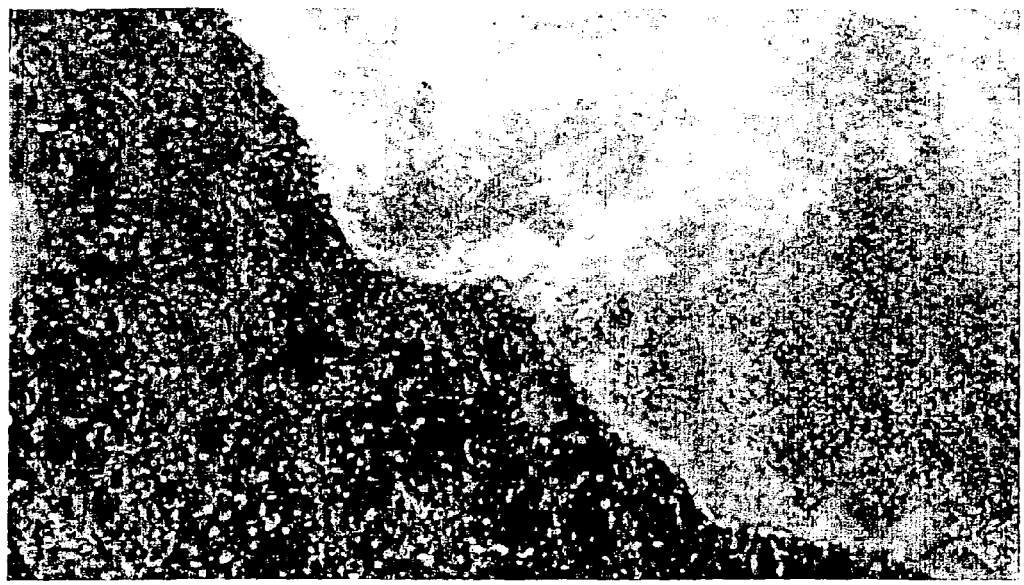
FIG. 8 (labeled 35-6): Edge of explanted stem cell colony photographed at 40× magnification. Original colony (0106992-2) plated from blastocyst activated week prior. Stem cell colony is top right. Mouse fetal fibroblast feeder layer is bottom left. Light is deflected showing difference in lipid content between the cells of the stem cell colony and the mouse fibroblast feeder layer.
Figure 9:
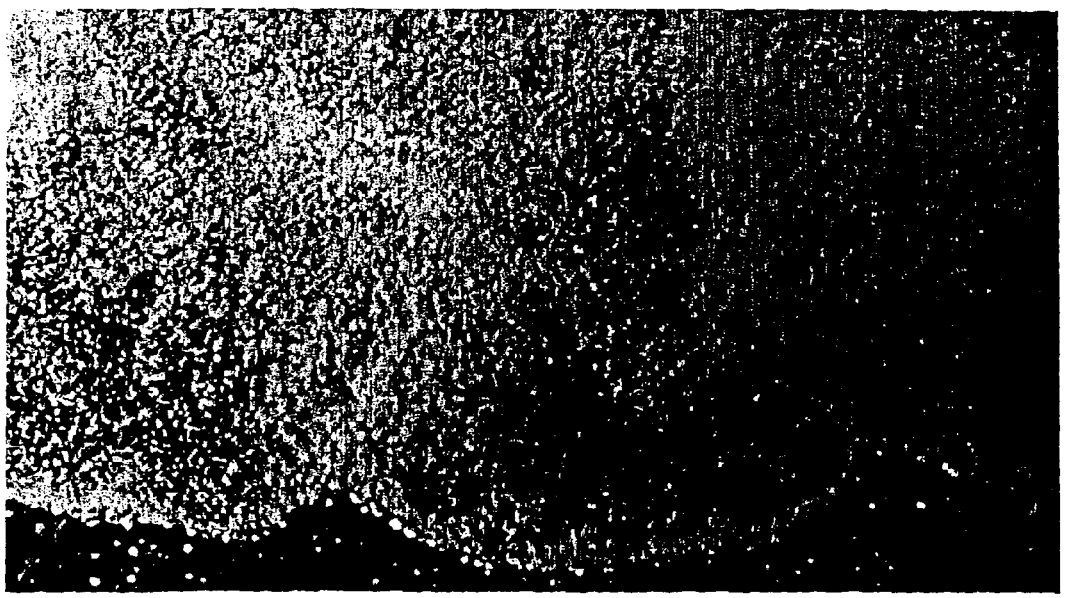
FIG. 9 (labeled 35-8): Edge of explanted stem cell colony photographed at 40× magnification. Original colony (0106992-2) plated from blastocyst activated week prior. Stem cell colony is on the top. Mouse fetal fibroblast feeder layer is on the bottom. Light is deflected showing difference in lipid content between the cells of the stem cell colony and the mouse fibroblast feeder layer.

Prior to describing the invention in detail, the following terms are defined. Otherwise, all terms in this application have their ordinary art-recognized meaning.

A. DEFINITIONS

Gynogenesis—
in the present invention this refers to the production of an embryo containing a discernible trophectoderm and inner cell mass that results upon activation of a cell, preferably an oocyte, or other embryonic cell type, containing mammalian DNA of all female origin, preferably human female origin, e.g., human or non-human primate oocyte DNA. Such female mammalian DNA may be genetically modified, e.g., by insertion, deletion or substitution of at least one DNA sequence, or may be unmodified. For example, the DNA may be modified by the insertion or deletion of desired coding sequences, or sequences that promote or inhibit embryogenesis. Typically, such embryo will be obtained by in vitro activation of an oocyte that contains DNA of all female origin. Gynogenesis is inclusive of parthenogenesis which is defined below. It also includes activation methods wherein the sperm or a factor derived therefrom initiates or participates in activation, but the spermatozoa! DNA does not contribute to the DNA in the activated oocyte.

Androgenesis—
in the present invention this refers to the production of an embryo containing a discernible trophectoderm and inner cell mass that results upon activation of an oocyte or other embryonic cell type, e.g., blastomere, that contains DNA of all male origin, e.g., human spermatozoal DNA. Optionally, said DNA of all male origin may be genetically modified, e.g., by the addition, deletion, or substitution of at least one DNA sequence (as described above with respect to gynogenesis).

Parthenogenesis—
the process by which activation of the oocyte occurs in the absence of sperm penetration. In the present invention, parthenogenesis refers to the development of an early stage embryo comprising trophectoderm and inner cell mass that is obtained by activation of an oocyte or embryonic cell, e.g., blastomere, comprising DNA of all female origin.

Pluripotent Cell—
in the present invention this refers to a cell derived from a embryo produced by activation of a cell containing DNA of all female or male origin that can be maintained in vitro for prolonged, theoretically indefinite period of time in an undifferentiated state, that can give rise to different differentiated tissue types, i.e., ectoderm, mesoderm, and endoderm. The pluripotent state of said cells is preferably maintained by culturing inner cell mass or cells derived from the inner cell mass of an embryo produced by androgenetic or gynogenetic methods under appropriate conditions, preferably by culturing on a fibroblast feeder layer or another feeder layer or culture that includes leukemia inhibitory factor. The pluripotent state of such cultured cells can be confirmed by various methods, e.g., (I) confirming the expression of markers characteristic of pluripotent cells; (ii) production of chimeric animals that contain cells that express the genotype of said pluripotent cells; (iii) injection of cells into animals, e.g., SCID mice, with the production of different differentiated cell types in vivo; and (iv) observation of the differentiation of said cells (e.g., when cultured in the absence of feeder layer or LIF) into embryoid bodies and other differentiated cell types in vitro.

Diploid Cell—
in the present invention, this typically refers to a cell, e.g., an oocyte or blastomere, having a diploid DNA content of all male or female origin.

Haploid Cell—
in the present invention, this typically refers to a cell, e.g., an oocyte or blastomere having a haploid DNA content, wherein the haploid DNA is of all male or female origin.

Activation—
process wherein fertilized or unfertilized oocyte, preferably in metaphase II of meiosis undergoes a process typically including separation of the chromatid pairs, extrusion of the second polar body, resulting in an oocyte having a haploid number of chromosomes, each with one chromatid. In the present invention, activation refers to methods whereby a cell containing DNA of all male or female origin is induced to develop into an embryo that has a discernible inner cell mass and trophectoderm, which is useful for producing pluripotent cells but which is itself incapable of developing into a viable offspring. Preferably, in the present invention, activation is preferably effected under one of the following conditions: (I) conditions that' do not cause second polar body extrusion; (ii) conditions that cause polar body extrusion but wherein polar body extrusion is inhibited; or (iii) conditions that inhibit first cell division of haploid oocyte. Also, the present invention includes activation of oocytes or blastomeres that have been transplanted with two male or two female haploid nuclei.

Metaphase II—
stage of cell development wherein the DNA content of a cell consists of a haploid number of chromosomes with each chromosome represented by two chromatids.

Embryo—
in the present invention this typically refers to an embryo that results upon activation of a cell, e.g., oocyte or other embryonic cells containing DNA of all male or female origin, which optionally may be modified, that comprises a discernible trophectoderm and inner cell mass, which cannot give rise to a viable offspring and wherein the DNA is of all male or female origin. The inner cell mass or cells contained therein are useful for the production of pluripotent cells as defined previously.

Inner Cell Mass—
inner portion of an embryo which gives rise to fetal tissues. Herein, these cells are used to provide a continuous source of pluripotent cells in vitro. In the present invention, the inner cell mass refers to the inner portion of the embryo that results from androgenesis or gynogenesis, i.e., embryos that result upon activation of cells containing DNA of all male or female origin. Preferably, such DNA will be human DNA, e.g., human oocyte or spermatozoa) DNA, which optionally has been genetically modified.

Trophectoderm—
other portion of early stage embryo which gives rise to placental tissues. In the present invention, the trophectoderm is that of an embryo that results from androgenesis or gynogenesis, i.e., embryos that result from activation of cells that contain DNA of all male or female origin, e.g., human oocyte or spermatozoan.

Differentiated Cell—
a non-embryonic cell that possesses a particular differentiated, i.e., non-embryonic state. The three earliest differentiated cell types are endoderm, mesoderm and ectoderm.

B. DETAILED DESCRIPTION

The present invention provides novel methods for obtaining pluripotent cells and cell lines, wherein the DNA is derived from a single individual, i.e., male or female, by androgenesis or gynogenesis.

In the native environment, immature oocytes (eggs) from the ovary undergo a process of maturation which results in the progression through meiosis to metaphase II of meiosis. The oocytes then arrest at metaphase II. In metaphase II, the DNA content of the cell consists of a haploid number of chromosomes, each represented by two chromatids.

Normally, the oocyte is ovulated at this stage and fertilized by the sperm. The sperm initiates the completion of meiosis in a process called activation. During activation, the pairs of chromatids separate, the second polar body is extruded, and the oocyte retains a haploid number of chromosomes, each with one chromatid. The sperm contributes the other haploid complement of chromosomes to make a full diploid cell with single chromatids. The chromosomes then progress through DNA synthesis during the first cell cycle. These cells then develop into embryos.

By contrast, in the present invention, embryos are developed by artificial activation of cells, typically mammalian oocytes or blastomeres containing DNA of all male or female origin. As discussed in the background of the invention, many methods have been reported in the literature for artificial activation of unfertilized oocytes. Such methods include physical methods, e.g., mechanical methods such as pricking, manipulation or oocytes in culture, thermal methods such as cooling and heating, repeated electric pulses, enzymatic treatments, such as trypsin, pronase, hyaluronidase, osmotic treatments, ionic treatments such as with divalent cations and calcium ionophores, the use of anaesthetics such as ether, ethanol, tetracaine, lignocaine, procaine, phenothiazine, tranquilizers such as thioridazine, trifluoperazine, fluphenazine, chlorpromazine, the use of protein synthesis inhibitors such as cycloheximide, puromycin, the use of phosphorylation inhibitors, e.g., protein kinase inhibitors such as DMAP, combinations thereof, as well as other methods.

Such activation methods are well known in the art and are discussed in our earlier patent application, U.S. Ser. No. 08/781,752, now U.S. Pat. No. 5,945,577. This application is incorporated by reference in its entirety herein.

In the present invention, a mammalian cell, preferably in metaphase II, typically an oocyte or blastomere comprising DNA of all male or female origin is artificially activated by a known means for effecting artificial activation of oocytes or nuclear transfer fusions. Dependent upon the activation procedure, the cell may extrude the second polar body or retain the second polar body.

In one embodiment of the present invention, a mammalian cell, preferably in metaphase II, e.g., a mammalian oocyte containing haploid content of DNA of all male or female origin is activated by an activation procedure that does not result in second polar body extrusion. This can be effected by various methods including the use of a phosphorylation inhibitor such as DMAP or by use of a micro filament inhibitor such as cytochalasin B, C or D, or a combination thereof. Thereby, cells are obtained having a diploid content of DNA of either male or female origin which develop into an embryo having a discernible trophectoderm and inner cell mass which will not give rise to viable offspring. The inner cell mass or cells therein are used to produce pluripotent cells containing cultures which are themselves useful for making differentiated cells and tissues.

In a second embodiment of the invention, a haploid cell, preferably in metaphase II, typically an oocyte or blastomere that comprises all male or female DNA, will be activated under conditions that result in the production of an embryo having a discernible trophectoderm and inner cell mass, but wherein the first cleavage event is prevented, thereby resulting in a diploid cell which develops into an embryo that cannot give rise to an offspring.

Still alternatively, the invention includes the embodiment wherein an enucleated cell, e.g., mammalian oocyte or blastomere, or other mammalian cytoplast, is transplanted with two male or female haploid nuclei, e.g., derived from oocytes or sperm, and is activated by an appropriate activation procedure to produce an embryo containing a discernible trophectoderm and inner cell mass which is incapable of giving rise to an offspring. Again, the inner cell mass or cells derived therefrom are useful for obtaining pluripotent cells which may be maintained for prolonged periods in tissue culture.

In all cases, the activated cell, e.g., oocyte, which is diploid, is allowed to develop into an embryo that comprises a trophectoderm and an inner cell mass. This can be effected using known methods and culture media that facilitate blastocyst development. Examples thereof are disclosed in our earlier patent application, U.S. Pat. No. 5,945,577, and have been well reported in the literature. Culture media suitable for culturing and maturation of embryos are well known and include Ham's F10+10% fetal calf serum, Tissue Culture Medium, 199 (TCM-199)+10% fetal calf serum, Tyrodes-Albumin-Lactate-Pyruvate (TALP), Dulbecco's Phosphate Buffered Saline (PBS), Eaglets and Whitten's media, and CR1 medium. A preferred medium is for bovine embryos TCM-199 with Earl salts, 10% fetal calf serum, 0.2 mM Na pyruvate and 50 µg/ml gentamycin sulfate. A preferred medium for culturing pig embryos is NCSU23.

Preferred medium for culturing primate embryos, e.g., human and nonhuman primate embryos, include modified Ham's F-10 medium (Gibco, Catalog No. 430-1200 EB) supplemented with 1 ml/L, synthetic serum replacement (SSR-2, Medl-Cult Denmark), and 10 mg/ml HSA; 80% Dulbecco's modified Eaglet's medium (DMEA, no pyruvate, high glucose formulation, Gibco BRL) with 20% fetal bovine serum, 0.1 mM B-mercaptoethanol, and 1% non-essential amino acid stock, and by methods and medium disclosed in Jones et al, *Human Reprod.* 13(1):169-177 (1998); Thomson et al, *Proc. Natl. Acad. Sci., USA,* 92:7894-7898 (1995); and Thomson et al, *Science,* 282:1145-1147 (1998); and two media available from Irvine Scientific, Santa Anna, Calif., i.e., a first media called P-1 (Cat. #99242) which is used for the first three days of culture followed by a second media, P-2 (Cat. #99292) until blastocyst stage.

Suitable activation conditions for human oocytes which may be applicable herein include the following:
1. Activation by Ionomycin and DMAP
(i)
a. Place oocytes in Ionomycin (5 µM) with 2 mM of DMAP for four minutes.
b. Move the oocytes into culture media with 2 mM of DMAP for four hours.
c. Rinse four times and place in culture.
(ii)
a. Place oocytes 22 to 28 hours post-maturation in 2 mM of DMAP.
b. After one hour, transfer to 5 µM of ionomycin.
c. After 3 to 5 minutes, transfer and incubate in 5 µg/ml of cytochalasm B and 10 µg/ml of cyloheximide for eight hours.
2. Activation by Ionomycin DMAP and Roscovitin
a. Place oocytes in Ionomycin (5 µm) with 2 mM of DMAP for four minutes.
b. Move the oocytes into culture media with 2 mM of DMAP and 200 microM of Roscovitin for three hours.
c. Rinse four times and place in culture.

3. Activation by Exposure to Ionomycin Followed by Cytochalasin and Cycloheximide.
a. Place oocytes in Ionomycin (5 microM) for four minutes.
b. Move oocytes to culture media containing 5 µg/ml of cytochalasin 13 and 5 µg/ml of cycloheximide for five hours.
c. Rinse four times and place in culture.
4. Activation by Electrical Pulses
a. Place eggs in mannitol media containing 100 µM $CaCL_2$
b. Deliver three pulses of 1.0 $kVcm^{-1}$ for 20 µsecond, each pulse 22 minutes apart.
c. Move oocytes to culture media containing 5 µg/ml of cytochalasin B for three hours.
5. Activation by Exposure with Ethanol Followed by Cytochalasin and Cycloheximide
a. Place oocytes in 7% ethanol for one minute.
b. Move oocytes to culture media containing 5 µg/ml of cytochalasin B and 5 µg/ml of cycloheximide for five hours.
c. Rinse four times and place in culture.
6. Activation by Microinjection of Adenophostin
a. Inject oocytes with 10 to 20 picoliters of a solution containing 10 µM of adenophostin.
b. Place oocytes in culture.
7. Activation by Microinjection of Sperm Factor
a. Inject oocytes with 10 to 20 picoliters of sperm factor isolated either from primates, pigs, bovine, sheep, goat, horse, mice, rat, rabbit or hamster.
b. Place eggs in culture.
8. Activation by Microinjection of Recombinant Sperm Factor After the androgenetic or gynogenetic embryos have been cultured to produce a discernable trophectoderm and inner cell mass, the cells of the inner cell mass are then used to produce the desired pluripotent cell lines. This can be accomplished by transferring cells derived from the inner cell mass or the entire inner cell mass onto a culture that inhibits differentiation. This is preferably effected by transferring said inner cell mass cells onto a feeder layer that inhibits differentiation, e.g., fibroblasts or epithelial cells, such as fibroblasts derived from murines, ungulates, chickens, such as mouse or rat fibroblasts, 570 and SI-m220 feeder cells, BRL cells, etc., or other cells that produce LIF. Preferably, the inner cell mass cells are cultured on mouse fetal fibroblast cells or other cells which produce leukemia inhibitory factor, or in the presence of leukemia inhibitory factor. Culturing will be effected under conditions that maintain said cells in an undifferentiated, pluripotent state, for prolonged periods, theoretically indefinitely.

Suitable conditions for culturing pluripotent cells, specifically pluripotent cells derived from ungulate inner cell mass are also described in our earlier U.S. Pat. No. 5,945,577, as well as U.S. Pat. No. 5,905,042, both of which are incorporated by reference herein in their entirety.

As noted, the subject invention will give rise to pluripotent cells having DNA that is exclusively of male or female origin, which may be used to produce different differentiated cell types.

In a preferred embodiment, such exclusively male or female DNA will be genetically modified before or after activation of the cell containing same, e.g., human oocyte.

Methods and materials for effecting genetic modification are well known and include microinjection, the use of viral DNAs, homologous recombination, etc. Thereby, pluripotent cells are obtained that comprise a desired DNA modification, e.g., contain a desired coding sequence.

The novelty of the invention is in the production of pluripotent cells that contain either female- or male-derived DNA. To the inventors' knowledge, this has not been reported for any species. Considerable work has been done in the mouse with pluripotent and totipotent embryonic stem cells but these have all been derived from either normal embryonic cells or primordial germ cells. Each of these cell types has both paternal and maternal DNA. Work has also been done with embryos containing either male-derived or female-derived DNA. These studies indicate that for full development of an embryo to term the cells must contain both male- and female-derived DNA. Imprinting of the DNA during meiosis results in some chromosomal segments being inactivated. Interestingly, if the cells are combined with normal embryonic cells in a chimera they do have the ability to form all the various cell types in the body. What has not been done for any species is the derivation of pluripotent cell lines containing only female- or male-derived DNA. Furthermore, no one has shown that these cells are capable of differentiation in culture.

An important feature of these cells is they would be immunologically similar, although not identical to the individual from which the DNA came. Consequently, they would also be the most immunologically compatible cells that could be obtained from an individual without the use of cloning. Furthermore, they would not generate the ethical concerns that the use of a normal embryo would generate because they could contain DNA from a single individual and would not be capable of forming an offspring.

However, another contemplated application of these cells and cell lines and differentiated cells derived therefrom is as donor cells for nuclear transfer, e.g. by the methods reported in U.S. Pat. No. 5,945,577 or patents and patent applications by the Roslin Institute. Essentially, these methods differ in that the ACT cloning methods utilize proliferating donor cells, e.g. mammalian somatic cells, such as fibroblasts, whereas the Roslin Institute methods utilize quiescent donor cells.

The pluripotent state of the cells produced by the present invention can be confirmed by various methods.

For example, the cells can be tested for the presence or absence of characteristic ES cell markers. In the case of human ES cells, examples of such markers are identified supra, and include SSEA-4, SSEA-3, TRA-1-60 and TRA-1-81 and are known in the art.

Also, pluripotency can be confirmed by injecting the cells into a suitable animal, e.g., a SCID mouse, and observing the production of differentiated cells and tissues. Still another method of confirming pluripotency is using the subject pluripotent cells to generate chimeric animals and observing the contribution of the introduced cells to different cell types. Methods for producing chimeric animals are well known in the art and are described in our related applications, incorporated by reference herein.

Yet another method of culturing pluripotency is to observe their differentiation into embryoid bodies and other differentiated cell types when cultured under conditions that favor differentiation (e.g., removal of fibroblast feeder layers). This method has been utilized in the present invention and it has been confirmed that the subject pluripotent cells give rise to embryoid bodies and different differentiated cell types in tissue culture. For example, it has been shown that Cynomolgous pluripotent cell lines produced herein give rise to beating cardiomyctes and other cells when allowed to differentiate by culturing of the cell line beyond confluency.

The resultant pluripotent cells and cell lines, preferably human pluripotent cells and cell lines, which are derived from DNA of entirely male or female original, have numerous therapeutic and diagnostic applications. Most especially, such pluripotent cells may be used for cell transplantation therapies or gene therapy (if genetically modified). Human ES cells have application in the treatment of numerous disease conditions.

In this regard, it is known that mouse embryonic stem (ES) cells are capable of differentiating into almost any cell type, e.g., hematopoietic stem cells. Therefore, human or other mammalian pluripotent (ES) cells produced according to the invention should possess similar differentiation capacity. The pluripotent cells according to the invention will be induced to differentiate to obtain the desired cell types according to known methods. For example, human ES cells produced according to the invention may be induced to differentiate into hematopoietic stem cells, muscle cells, cardiac muscle cells, liver cells, cartilage cells, epithelial cells, urinary tract cells, etc., by culturing such cells in differentiation medium and under conditions which provide for cell differentiation. Medium and methods which result in the differentiation of ES cells are known in the art as are suitable culturing conditions.

For example, Palacios et al, *Proc. Natl. Acad. Sci., USA*, 92:7530-7537 (1995) teaches the production of hematopoietic stem cells from an embryonic cell line by subjecting stem cells to an induction procedure comprising initially culturing aggregates of such cells in a suspension culture medium lacking retinoic acid followed by culturing in the same medium containing retinoic acid, followed by transferral of cell aggregates to a substrate which provides for cell attachment.

Moreover, Pedersen, *J. Reprod. Fertil. Dev.*, 6:543-552 (1994) is a review article which references numerous articles disclosing methods for in vitro differentiation of embryonic stem cells to produce various differentiated cell types including hematopoietic cells, muscle, cardiac muscle, nerve cells, among others.

Further, Bain et al, *Dev. Biol.*, 168:342-357 (1995) teaches in vitro differentiation of embryonic stem cells to produce neural cells which possess neuronal properties. These references are exemplary of reported methods for obtaining differentiated cells from embryonic or stem cells. These references and in particular the disclosures therein relating to methods for differentiating embryonic stem cells are incorporated by reference in their entirety herein.

Thus, using known methods and culture medium, one skilled in the art may culture the subject ES cells, including genetically engineered or transgenic ES cells, to obtain desired differentiated cell types, e.g., neural cells, muscle cells, hematopoietic cells, etc.

Pluripotent cells produced by the invention may be used to obtain any desired differentiated cell type. Therapeutic usages of differentiated human cells are unparalleled. For example, human hematopoietic stem cells may be used in medical treatments requiring bone marrow transplantation. Such procedures are used to treat many diseases, e.g., late stage cancers such as ovarian cancer and leukemia, as well as diseases that compromise the immune system, such as AIDS. Hematopoietic stem cells can be obtained, e.g., by incorporating male or female DNA derived from a male or female cancer or AIDS patient with an enucleated oocyte, obtaining pluripotent cells as described above, and culturing such cells under conditions which favor differentiation, until hematopoietic stem cells are obtained. Such hematopoietic cells may be used in the treatment of diseases including cancer and AIDS.

Alternatively, the subject pluripotent cells may be used to treat a patient with a neurological disorder by culturing such cells under differentiation conditions that produce neural cell lines. Specific diseases treatable by transplantation of such human neural cells include, by way of example, Parkinson's disease, Alzheimer's disease, ALS and cerebral palsy, among others. In the specific case of Parkinson's disease, it has been demonstrated that transplanted fetal brain neural cells make the proper connections with surrounding cells and produce dopamine. This can result in long-term reversal of Parkinson's disease symptoms.

The great advantage of the subject invention is that it provides an essentially limitless supply of pluripotent, preferably pluripotent human cells that can be used to produce differentiated cells suitable for transplantation. Such cells should alleviate the significant problem associated with current transplantation methods, i.e., rejection of the transplanted tissue which may occur because of host-vs-graft or graft-vs-host rejection. Conventionally, rejection is prevented or reduced by the administration of anti-rejection drugs such as cyclosporin. However, such drugs have significant adverse side-effects, e.g., immunosuppression, carcinogenic properties, as well as being very expensive. The present invention should eliminate, or at least greatly reduce, the need for anti-rejection drugs.

Other diseases and conditions treatable by cell therapy include, by way of example, spinal cord injuries, multiple sclerosis, muscular dystrophy, diabetes, liver diseases, i.e., hypercholesterolemia, heart diseases, cartilage replacement, burns, foot ulcers, gastrointestinal diseases, vascular diseases, kidney disease, urinary tract disease, and aging related diseases and conditions.

This methodology can be used to replace defective genes, e.g., defective immune system genes, cystic fibrosis genes, or to introduce genes which result in the expression of therapeutically beneficial proteins such as growth factors, lymphokines, cytokines, enzymes, etc. For example, the gene encoding brain derived growth factor may be introduced into human pluripotent cells produced according to the invention, the cells differentiated into neural cells and the cells transplanted into a Parkinson's patient to retard the loss of neural cells during such disease.

Previously, cell types transfected with BDNF varied from primary cells to immortalized cell lines, either neural or non-neural (myoblast and fibroblast) derived cells. For example, astrocytes have been transfected with BDNF gene using retroviral vectors, and the cells grafted into a rat model of Parkinson's disease (Yoshimoto et al., *Brain Research*, 691:25-36, (1995)).

This ex vivo therapy reduced Parkinson's-like symptoms in the rats up to 45% 32 days after transfer. Also, the tyrosine hydroxylase gene has been placed into astrocytes with similar results (Lundberg et al., *Develop. Neurol.*, 139:39-53 (1996) and references cited therein).

However, such ex vivo systems have problems. In particular, retroviral vectors currently used are down-regulated in vivo and the transgene is only transiently expressed (review by Mulligan, Science, 260:926-932 (1993)). Also, such studies used primary cells, astrocytes, which have finite life span and replicate slowly. Such properties adversely affect the rate of transfection and impede selection of stably transfected cells. Moreover, it is almost impossible to propagate a large population of gene targeted primary cells to be used in homologous recombination techniques. By contrast, the difficulties associated with retroviral systems should be eliminated by the use of the methods herein.

Genes which may be introduced into the subject pluripotent cells include, by way of example, epidermal growth factor, basic fibroblast growth factor, glial derived neurotrophic growth factor, insulin-like growth factor (I and II), neurotrophin-3, neurotrophin-4/5, ciliary neurotrophic factor, AFT-1, cytokine genes (interleukins, interferons, colony stimulating factors, tumor necrosis factors (alpha and beta), etc.), genes encoding therapeutic enzymes, etc.

In addition to the use of human pluripotent cells and cells derived therefrom in cell, tissue and organ transplantation, the present invention also includes the use of non-human cells in the treatment of human diseases. For example, non-human primate pluripotent cells produced according to the invention should be useful for treatment of human disease conditions where cell, tissue or organ transplantation is warranted (given the phylogenetic closeness of primates and humans (immunogenicity should be less of a concern.) In general, pluripotent cells and differentiated cells derived therefrom produced according to the present invention can be used within the same species (autologous, syngenic or allografts) or across species (xenografts). For example, brain cells derived from bovine or porcine pluripotent cells may be used to treat Parkinson's disease.

Also, the subject pluripotent ES cells, preferably human cells, may be used as an in vitro model of differentiation, in particular for the study of genes which are involved in the regulation of early development. Also, differentiated cell tissues and organs produced using the subject ES cells may be used in drug studies.

Further, the subject ES cells or differentiated cells derived therefrom may be used as nuclear donors for the production of other ES cells and cell colonies, or in the case of non-human cells, for the production of cloned animals.

Still further, pluripotent cells obtained according to the invention may be used to identify proteins and genes that are involved in embryogenesis. This can be effected e.g. by differential expression, i.e. by comparing mRNA's that are expressed in pluripotent cells provided according to the invention to mRNAs that are expressed as these cells differentiate in to different cell types, e.g., neural cells, myocardiocytes, other muscle cells, skin cells, etc. Thereby, it may be possible to determine what genes are involved in differentiation of specific cell types.

Also, it is another object of the invention to expose pluripotent cell lines produced according to the invention to cocktails of different growth factors, at different concentrations so as to identify conditions that induce the production and proliferation of desired differentiated cell types.

In order to more clearly describe the subject invention, the following example is provided.

Example 1

Production of Pluripotent Cells by Activation of Bovine Oocytes Containing DNA of Female Origin The example describes one method of producing pluripotent cells by androgenetic or gynogenetic activation and production of embryos. In particular, this example describes the production of pluripotent cells from parthenogenetically activated bovine oocytes (gynogenetic activation of bovine oocytes containing all female DNA effected using ionomycin and DMAP). As described below, and substantiated by FIGS. 1 through 10, this procedure resulted in the production of an embryo having a discernible trophectoderm and inner cell mass, the inner cell mass of which, when cultured on a mouse fetal fibroblast feeder layer gave rise to pluripotent cells which produce differentiated cells (See especially FIG. 10).

TABLE 2

Materials and Methods Used in Example
Media and Solutions

| Hyluronidase (0.01% solution) | | |
|---|---|---|
| Hyluronidase | (Sigma H-3506) | 1 mg |
| DBS | | 1 ml |
| TL Hepes | | |
| NaCNaCl | (Sigma S-5886) | 666 mg |
| KCl | (Sigma P-5404) | 24 mg |
| NaHCO$_3$ | (Sigma S-5761) | 16.8 mg |
| NaH$_2$PO$_4$—H$_2$O | (Sigma S-9638) | 4.76 mg |
| Hepes | (Sigma H-9136) | 240 mg |
| Na Lactate (60% syrup) | (Sigma L-1375) | 186 41 |
| Phenol Red (0.5% solution) | (Sigma P-0290) | 100 pi |
| CaCl$_2$—2H$_2$O | (Sigma C-7902) | 300 mg |
| MgCl$_2$6H$_2$O | (Sigma M-2393) | −5 mg |
| Embryo transfer H$_2$O | (Sigma W-1503) | enough to make final volume 100 ml |

Adjust pH to 7.3-7.4
Filter with 0.2 pm filter and place in 50 ml capped bottle, label and date.
Store buffer at 4° C.

| HECM Hepes | | |
|---|---|---|
| NaCl | (Sigma S-5886) | 0.662 g |
| KCl | (Sigma P-5405) | 0.0239 g |
| CaCl$_2$—2H$_2$O | (Sigma C-7902) | 0.0294 g |
| MgCl$_2$—6H$_2$O | (Sigma M-2393) | 0.0102 g |
| BME-ammino acids | (Sigma B-6766) | 1 ml |
| Na Lactate | (Sigma L-1375) | 1.4 ml |
| Na Pyruvate | (Sigma P-2256) | 0.011 g |
| NaHCO$_3$ | (Sigma S-5761) | 0.168 g |
| Hepes | (Sigma H-9136) | 0.238 g |
| Phenol Red | (Sigma P-0290) | 0.1 ml |
| Pen/Strep | (Sigma P-3539) | 1 ml |
| BSA fraction V | (Sigma A-4503) | 0.3 g |
| Embryo transfer H$_2$O | (Sigma W-1503) | enough to make final |

TABLE 2-continued

Materials and Methods Used in Example
Media and Solutions

|  |  | volume 100 ml |
| --- | --- | --- |

Osmolarity must be 275 +/− 10 mOsm/kg
Adjust pH to 7.3-7.4
Filter with 0.2 um filter and place in 50 ml capped bottle, label and date.
Store buffer at 4° C.

ACM Media

| NaCl | (Sigma S-5886) | 0.290 g |
| --- | --- | --- |
| KCl | (Sigma P-5405) | 0.011 g |
| CaCl2—2H20 | (Sigma C-7902) | 0.002 g |
| NaHCO3 | (Sigma S-5761) | 0.105 g |
| Na Lactate | (Sigma L-4263) | 71_11 |
| Pyruvate stock |  | 1 ml |
| BME amino acids | (Sigma B-6766) | 1 ml |
| MEM amino acids | (Sigma M-7145) | 0.5 ml |
| L-Glutamine | (Sigma G-5763) | .7.3 mg |
| Pen/Strep | (Sigma P-3539) | 0.5 p.1 |
| BSA fraction V | (Sigma A-4503) | 150 g |
| Embryo transfer $H_2O$ | (Sigma W-1503) | enough to make final volume 50 ml |

Adjust pH to 7.3-7.4
Filter with 0.2 um filter and place in 50 ml capped bottle, label and date.
Store buffer at 4° C.

Pyruvate Stock

| Pyruvic Acid | (Sigma P-2256) | 2.2 mg |
| --- | --- | --- |
| Embryo transfer $H_2O$ | (Sigma W-1503) | 1 ml |

Label and store at −20° C. in 1 ml aliquots.

Ionomycin

| Ionomycin | (Calbiochem 407952 or (Sigma 1-0634) | 1 mg |
| --- | --- | --- |
| Dimethyl Sulfoxide | (Sigma D-8799) | 267.6 pi |

Label and store at −4° C. in 5 μl aliquots.
Z1
TL Hepes + 1 mg/ml BSA (fraction V), pH to 7.2-7.4.
Filter, label and store at 4° C. in a capped container.

DMAP 200 mM (100X stock)

| DMAP | (Sigma D-2629) | 1 g |
| --- | --- | --- |
| PBS | (Gibco 21600-051) | 30 ml |

Heat in boiling water bath to dissolve DMAP.
Aliquot 20 μl into small eppendorf tubes, label and date.
Store aliquots at −20° C.
Mouse Fetal Fibroblasts Feeder Layers
Mouse fetal fibroblasts are gamma irradiated for five minutes and plated at $1 \times 10^6$ cells per ml of ALPHA-MEM culture media. Leave overnight or until cells are plated and change media to desired culture media.

ALPHA-MEM Culture Media

| ALPHA-MEM | (Gibco 12-169F) | 500 ml |
| --- | --- | --- |
| Fetal Calf Serum | (HyClone A-111-D) | 50 ml |
| Antibiotic/Antimicotic | (Sigma A-7292) | 2 ml |
| 2-Mercaptoethanol | (Gibco 21985-023) | 1.4 ml |
| L-Glutamine Stock |  | 5 ml |
| Tylosine Tartrate | (Sigma G-5763) | 0.5 ml |

L-Glutamine Stock

| L-Glutamine | (Sigma G-5763) | 1.5 g |
| --- | --- | --- |
| DPBS |  | 50 ml |

Filter and aliquot 5.5-6.0 ml in 15 ml tubes.
Label and freeze on side.

Procedures—Oocyte Preparation

Bovine oocytes were stripped eighteen hours post maturation using 0.01% solution of hyluronidase (1 mg/ml) contained in TL Hepes media. Afterward, the stripped oocytes are rinsed using HECM Hepes or TL Hepes. The resultant stripped, rinsed oocytes are then stored or used directly for activation. Storage can be effected, e.g., in ACM at 37° C. and five percent $CO_2$ until activation. Preferably, the ACM is equilibrated at 37° C. and five percent $CO_2$ for about two to three hours before usage for oocyte storage.

Oocyte Activation

An appropriate activation protocol is used that results in the production of embryos having a discernible trophectoderm and inner cell mass. As previously disclosed, various methods can be used.

In particular, the inventors elected to effect activation by placing oocytes (prepared as above) in Z1 media containing 5 µM of ionomycin for four minutes. This media was prepared by diluting 2 µL of 5 mM ionomycin in 2 ml of Z1 medium.

Afterward, the oocytes were washed using HECM Hepes, and are then incubated in DMAP/ACM medium for three to four hours. This medium was prepared by dilution of 5 µL of 200 mM DMAP in 500 µl of ACM, with ACM/DMAP preferably being equilibrated at 37° C. and five percent $CO_2$ in air for two to three hours prior to usage.

After incubation in DMAP/ACM, oocytes were washed four times in HECM Hepes. The washed oocytes were then placed in ACM on a mouse fibroblast feeder layer prepared as described above. The ACM media was again equilibrated at 37° C. and five percent $CO_2$ in air for two to three hours prior to use.

This resulted in the production of blastocysts having a discernible trophectoderm and inner cell mass (See FIGS. 1 through 10). Seven to nine days post activation, the blastocysts were dissected using 30 gauge/1 inch needles and placed on mouse fetal fibroblast feeder layers in ALPHA-MEM tissue culture medium. The cells were incubated thereon at 37° C. and five percent $CO_2$ for one week.

The medium was changed every two to three days following said week of incubation.

Figure 10:
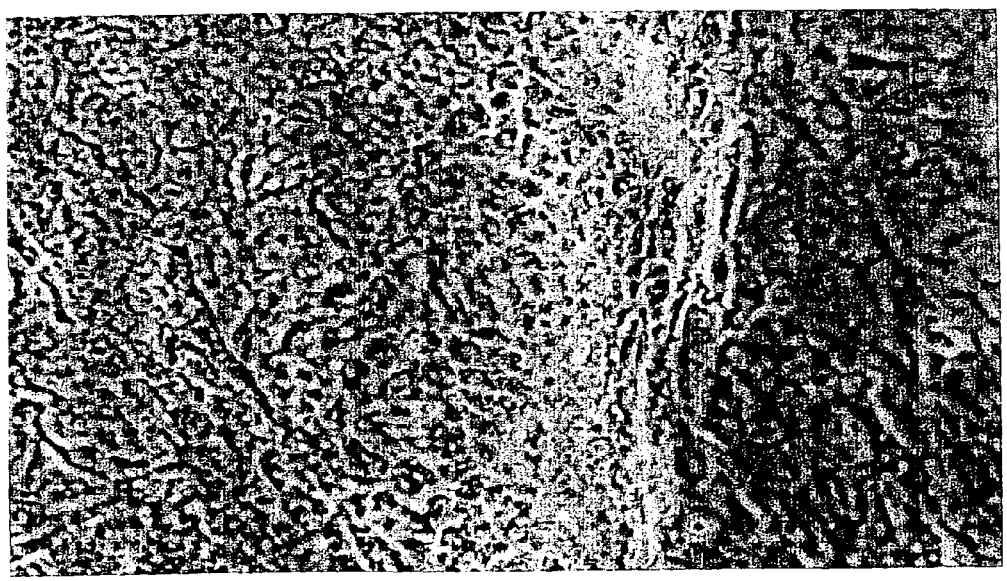
FIG. 10 (labeled 35-19): Edge of explanted stem cell colony photographed at 200× magnification. Original colony (0106992-2) plated from blastocyst activated week prior. Stem cell colony is on the left. Mouse fetal fibroblast feeder layer is on the right. Photograph shows differentiation of the cells at the edge of the stem cell colony.

The cells were passaged onto new feeder layers manually. This Was effected by culturing the colonies and pipetting directly the pieces onto new feeder layers. This procedure can be repeated by change of medium and repeated passaging indefinitely to produce pluripotent cells that give rise to differentiated cells. The efficacy of the described methods is substantiated by FIGS. 1 through 10. In particular, FIG. 10 shows a pluripotent cell colony produced from a blastocyst produced by gynogenetic (parthenogenic) activation as described above, resulted in a pluripotent (stem cell) colony with differentiated cells being observed at the edge of the colony.

Example 2

Production of Parthogenic Primate Primordial Stem Cells (PPSCs)

Materials and Methods

1-Cynomolgous Monkey (*Macaca fascicularis*) were superovulated using a single injection of 1000 IU of pregnant mare's serum gonadtrophin (PMSG) and 500 IU of human chorionic gonadoprophin (hCG) four days later.

2-Ovaries were retrieved by laparotomy and oocytes dissected from the follicles and placed in maturation media 36 to 48 hrs after (hCG). Maturation media consisted of medium-199 (Gibco BRL) with Earle's balanced salt solution supplemented with 20% fetal bovine serum, 10 11__1/ml of PMSG, 10111/ml of hCG, 0.05 mg/ml of penicillin G and 0.075 mg/ml of steptomycin sulfate (Hong, 1999).

3-Oocyte activation. After 40 hrs in maturation, metaphase II eggs were placed in 10 micromoles of Ionomycin followed incubation in 200 mM 6-DMAP (dimethylaminopurine) for 3 to 4 hrs.

4-Embryo culture. Commercially available embryo culture media 'Cooks' was used (modified SOF). Embryos were cultured with a co-culture of mitotically inactivated mouse embryonic fibroblasts as feeder layer.

5-Isolation of Inner Cell Mass
1-Upon development to blastocyst, embryos were placed in a buffered solution of 0.3% pronase for 2 minutes to digst zona pellucida
2-Blastocyts were then rinsed in buffered solution and moved to solution of GI culture media and polyclonal antibodies (antihuman whole serum) 1:3 dilution for 30 minutes.
3-Embryos were rinsed 5 times in a buffered solution.
4-Embryos were moved into a solution of GI culture media and guinea pig complement 1:3 dilution for 30 minutes.
5-Remaining of the embryos (dead trophoblast cells and ICM) were rinsed 5 times in buffered solution the Inner Cell Mass (ICM) was isolated and placed on top of a mouse embryonic fibroblast feeder layer for isolation and growth of Primordial Stem Cells (PSC's).

Results

We have obtained 450 eggs total, after maturation, 224 were still at germinal vesicle stage (GV=no maturation), 79 were dead, 56 were at metaphase one (MI) and 91 at metaphase two (MIT).

Figure 11:
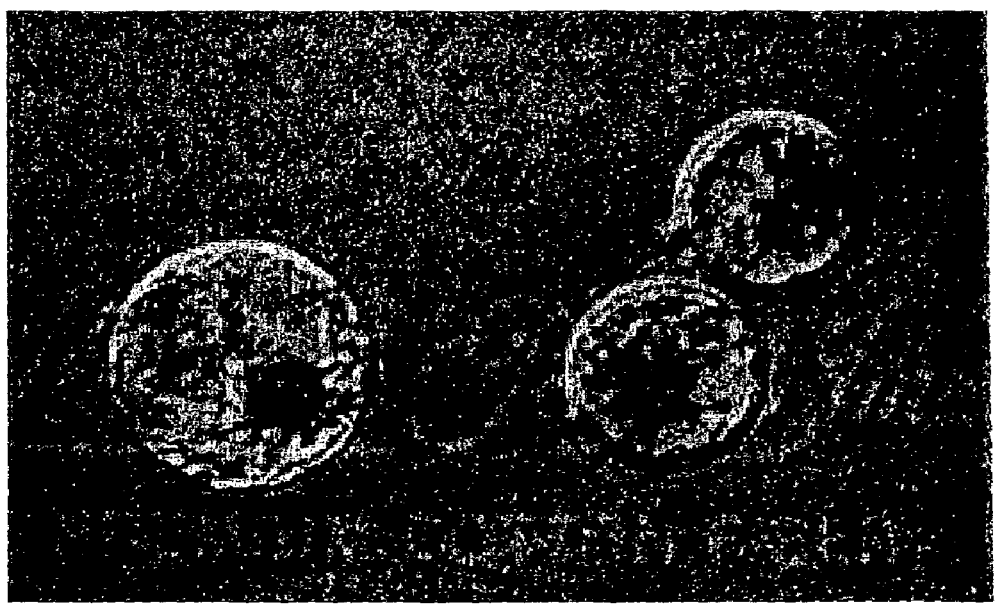
FIG. 11 shows three monkey blastocysts on day 8 of development.

We have parthenogenically activated all of them. As expected, there was no cleavage on the GV group, 32% cleavage on the MI and 57% on the MIL When put in culture, 7 embryos developed to the blastocyst stage (See FIG. 11).

Figure 12:
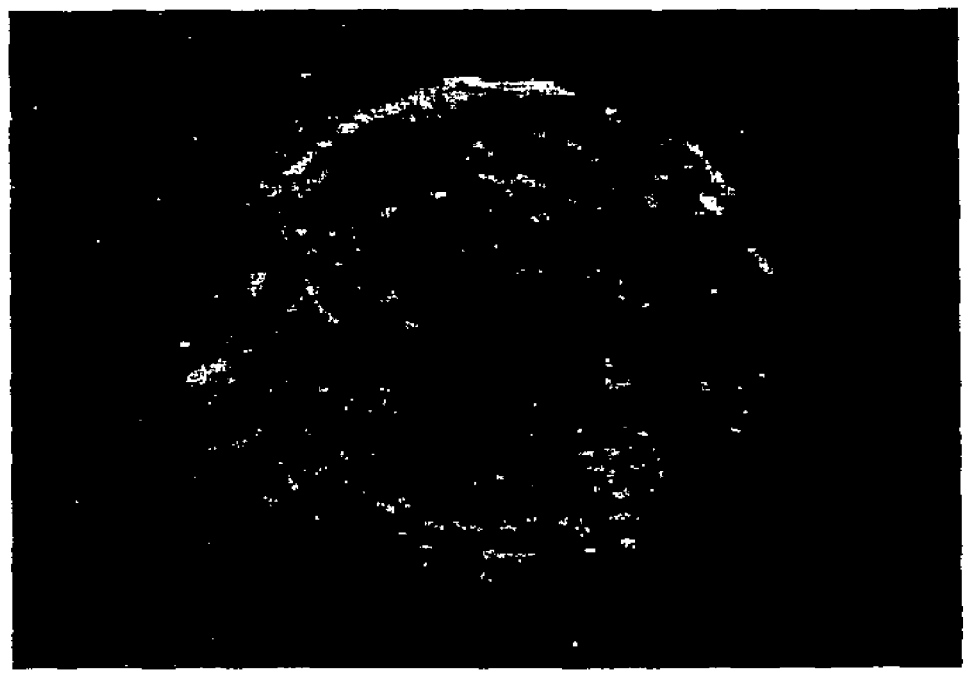
FIG. 12 shows a cell line (Cyno 1) obtained from one of the three monkey blastocytsts shown in FIG. 11, before immunosurgery.
Figure 13:
FIG. 13 shows the Cyno 1 cell line after immunosurgery.
Figure 14:
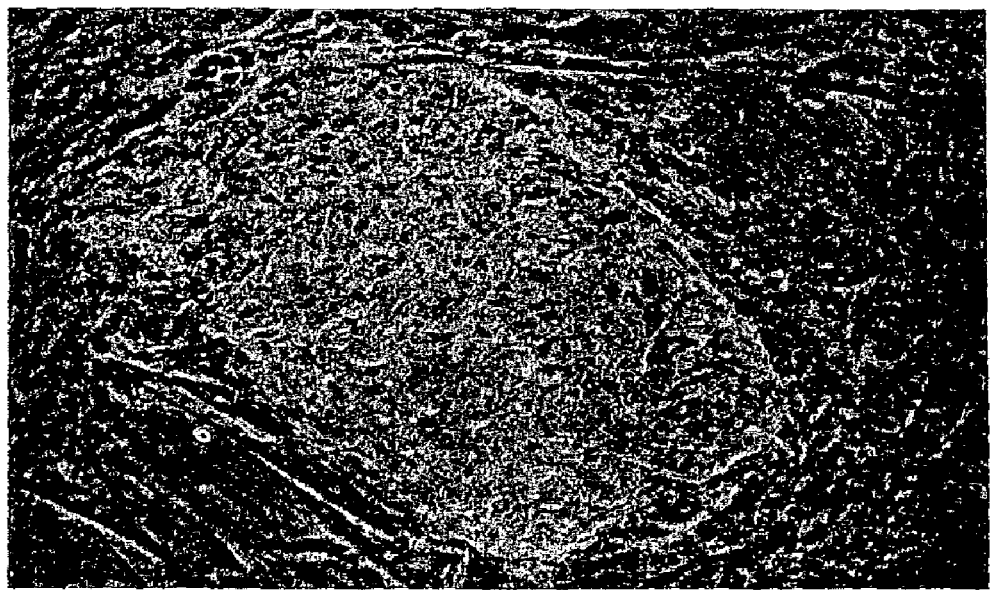
FIG. 14 shows the Cyno 1 cell line 5 days after plating on a fibroblast feeder layer.

After attempting to establish ES-like culture cells, four Inner cell masses attached nicely one differentiated immediately, and out of the three remaining, one cell line was obtained. This cell line is called Cyno 1 (FIG. 12). This cell line before and after immunosurgery is shown in FIGS. 12 and 13. FIG. 14 shows the Cyno 1 cell line five days after plating.

Figure 15:
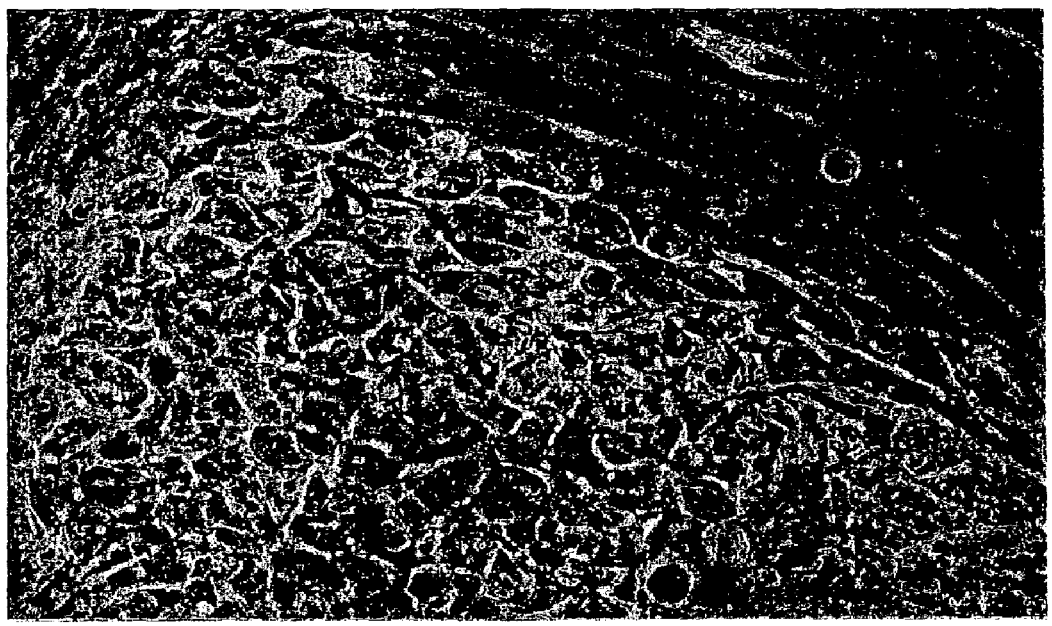
FIG. 15 shows a pluripotent cell line (referred to as Cyno 1) derived from a parthogenetically activated Cynomolgous monkey oocyte, growing on a mouse fibroblast layer. The feeder cells exhibit morphological characteristics of pluripotent cells, e.g. small nuclear cytoplasmic ratios and detectable cytoplasmic granules.

FIG. 15 shows the Cyno 1 cell line growing on top of a mouse fibroblast feeder layer. These cells show typical morphology of pluripotent-embryonic-cells such as small nuclear cytoplasmic ratio and the presence of cytoplasmic granules.

These cells were maintained in an undifferentiated state for a period of up to 11 months. This is evidenced by screening of such cells after prolonged culturing for the expression of a cell marker characteristic of undifferentiated cells, Alkaline Phosphatase. As expected, cells were positive on passage 3 and on passage 5.

Cyno-1 cells displayed many features that are typical for ES cells: Morphologically, the cells had a small cytoplasmic/nuclear ratio, numerous and prominent nucleoli and cytoplasmic lipid bodies. They could be extensively propagated in vitro while maintaining their undifferentiated state. These cells tested positive for alkaline phosphatase, and were immunoreactively positive for SSEA-4, TRA 1-60, TRA 1-81 and Oct-4, and negative for SSEA-1 and SSEA-3. The fact that Cyno-1 cells stain negatively for SSEA-3 physically distinguishes them from other primate and human stem cells described previously. Thomson et al., 1996, Biol. Reprod. 55(2):254-9; Thomson et al., 1998, Science-282(5391): 1145-7. In addition, karyotyping revealed 40+2 chromosomes as is expected for *Macaca fascicularis* (data not shown).

The fact that these cells maintain their pluripotency is also shown by their spontaneous differentiation into many differentiated cell types after being placed in tissue culture in the absence of a feeder layer. Differentiation of Cyno-1 cells was induced by allowing the cells to overgrow and by modifying culture conditions, i.e., by isolating the cells from the mouse feeder layer and culturing them in the presence of DMEM with 15% fetal calf serum, in some instances 1000 IU of LIF was added to the media. In the days following, the cells were observed to differentiate into cuboidal and ciliated epithelium, fibroblasts, beating myocardial cells, smooth muscle cells and cytokeratine-positive cells as well as neuronal cells. Two colonies of beating myocardial cells were observed in one well of a 4-well tissue culture plate.

Cyno-1-derived neural cells proliferated readily and expressed the CNS stem cell marker nestin (data not shown). They were also observed to differentiate into astrocytes or neurons depending on the culture conditions. The most remarkable differentiation observed in Cyno 1 cells was obtained when derived neural precursors were exposed to defined morphogenic factors. In this case, up to 25% of midbrain dopamine neurons was observed. This is a specialized population of neurons, whose efficient generation from primate embryonic stem cells has not been reported previously. Neuronal identity and function was confirmed by HPLC analysis measuring in vitro release of the neurotransmitters dopamine and serotonin (data not shown). Cyno-1 derived neurons exhibited both basal and KC1-evoked synaptic release of dopamine and serotonin.

In vivo random differentiation of Cyno-1 cells was tested by injecting them into the peritoneal cavity of immunocompromised SCID mice. Teratomas were isolated 8 and 15 weeks after injection and subjected to histological analysis. Derivatives of all three germ layers were observed including cartilage, muscle and bone (mesoderm), neurons, skin and hair follicles (ectoderm) and intestinal epithelia (endoderm). The presence of mature tissues and low frequency of mitotic figures in these tumors indicated their benign nature.

Telomerase activity is often correlated with replicative immortality. Telomerase is typically expressed in germ cells, cancer cells and a variety of stem cells, including embryonic stem cells, but absent in most somatic cell type. Undifferentiated Cyno-1 cells displayed high levels of telomerase activity as detected by the TRAP assay (TRAPEZE Kit, Intergen, N.Y.). However, no telomerase activity could be detected in differentiated progeny of Cyno-1 cells (data not shown). These data indicate a physiologically normal control of telomerase activity in Cyno-1 cells.

To determine whether differentiated cells of various somatic cell lineages were observed from the differentiating PPSCs, we extracted mRNA from differentiated cell cultures, performed RT-PCR, using human sequence primers specific for various differentiated cell types. As shown in FIG. 16, transcripts of a predicted size for the mesodermally-derived transcripts brachyury and skeletal muscle myosin heavy polypeptide 2 were observed. The transcript sonic hedgehog essential for endoderm development was observed. In addition, the neuron-specific ectoderm marker enolase was observed as well as keratin (not shown) as markers of ectodermally derived cells. These PCR products were not observed in the mouse feeder layer controls or in the absence of reverse transcriptase.

To establish that the imprinting status of parthogenetic PPSCs is different than that of di-parental PPSCs we looked at the expression of several imprinted genes. Genes that are mono-allelically expressed from the paternal allele, would not be expected to be expressed in parthogenetic cells, as these cells are derived exclusively from the maternal genome. The Snrpn gene is mono-allelically expressed from the paternal allele in mouse blastocyst inner cell mass [Szabo, P E and Mann, JR; *Genes & Development* 9:3097-3108 (1995)]. We looked at the expression of this gene in the parthogenetic *Macaca facicularis* PPSCs and found that the expression was undetectable by RT-PCR, whereas under identical conditions, this gene is readily detected in fibroblast cell cultures from the same species. The Snrpn gene is expected to be expressed in diparental PPSCs, as these cells contain a paternal allele. In FIG. 17, the expected size RT-PCR product for the Snrpn gene is 260 bp. Thus, Cyno-1 cells may provide a novel tool for assessing the effects of genomic imprinting on cell differentiation and function during development in primates.

DNA profiling of Cyno-1 cells was performed to confirm the identity of these cells with respect to the donor animal. Total genomic DNA from a cynomolgus monkey cell donor #5571 (Buttercup) and from a preparation of cultured stem cells (Cyno-1; derived from Buttercup) were genotyped and compared using 7 simple sequence repeat (SSR) human markers (Research Genetics, Inc.; Huntsville, Ala.) that had been shown previously to amplify monkey DNA and to discriminate between two individuals. The markers represent 7 different chromosomes (#3, 6, 7, 10, 11, 16 & 17) and in all cases except one (marker D16S403), alleles for Buttercup were identical in number and size to the alleles for the Cyno-1 cells. An additional test was performed on DNA from Buttercup and from the Cyno-1 cells (as well as 2 control animals). Micro SSPTM Generic HLA Class II DNA typing was performed in a 96 well tray format through the Wake Forest University—Baptist Medical Center Histocompatibility Laboratory. The data demonstrated that embryonic stem cells Cyno-1 and somatic cells from Buttercup were indistinguishable from each other and therefore should be considered autologous (data not shown).

The histocompatibility antigen profile of Cyno-1-derived neurons was investigated and compared to lymphocytes from the oocyte donor by investigating polymorphic genes within the major histocompatibility complex (MHC) that encode class 1 and class II cell surface proteins. These proteins present immunogenic peptides to $CD8^+$ and $CD4^+$ T cells, respectively. We have analyzed the Cyno-1-derived neural cells by flow cytometry for the expression of Mafa (MHC of *M. fascicularis*) class I and class II antigens. Peripheral blood lymphocytes (PBLs) from the original cell donor expressed class I and class II antigens detected by antibodies specific for monomorphic HLA-A, B, C and HLA-DR antigens, respectively (data not shown). Seventy-five percent of PBLs were positive for class 1 and 14% of PBLs were positive for class II. However, Cyno-1-derived neural cells were negative for both Mara class I and class II antigens, consistent with observations that these CNS cell types are class I- and class II-negative in normal murine central nervous system. Altintas, A., et al., Differential expression of H-2K and H-2D in the central nervous system of mice infected with Theiler's virus. J. Immunol., 1993. 151(5): p. 2803-12; Rodriguez, M., M. L. Pierce, and E. A. Howie, Immune response gene products (Ia antigens) on glial and endothelial cells in virus-induced demyelination. J. Immunol., 1987. 138(10): p. 3438-42.

Viral infection or treatment with interferon-gamma (IFNγ) stimulates upregulation of class I and class II expression by murine CNS cells. The ability of IFNγ to upregulate class I and class II expression by Cyno-1-derived neural cells was investigated by pre-culturing these cells with IFNγ (40 ng/ml) overnight prior to staining and flow cytometry. Pre-treatment of Cyno-1 derived cells resulted in class I-specific staining with an intensity that was comparable to staining of normal human PBLs. However, IFNγ treatment did not increase class II expression. These results support the prediction that an in vivo inflammatory response, expectedly involving IFNγ expression, would upregulate class I expression on transplanted Cyno-1-derived neural cells. Accordingly, in the event of transplantation into a non-isogenic animal, these cells should not escape surveillance by CD8$^+$ cytotoxic T lymphocytes.

In conclusion, we have generated a primate parthenogenetic cell line with ES-like properties that can be propagated in vitro in an undifferentiated state for at least 11 months. The in vitro derivation of large numbers of specific cell lineages from Cyno-1 cells, including the generation of unlimited numbers of dopaminergic neurons is of particular interest. Clinical transplantation of specific fetal neurons has shown promise in the treatment of Parkinson's and Huntington's disease but obtaining such cells from animals or human fetal brain remains problematic. Neurons derived in vitro from a renewable source such as CNS precursors, embryonic, or parthenogenetic animal or human stem cells, could alleviate some of the ethical and technical concerns of human cell therapy. In addition, Cyno-1 cells may be useful in the in vitro study of imprinting, early development, and for the isolation of embryonic proteins and cell components, useful in the reprogramming of human cells.

The protocols described here for parthenogenetic activation of human eggs, coupled with the derivation of primate parthenogenetic stem cells, are likely to be applicable for the generation of human parthenogenetic stem cells. As our understanding of fate determination advances, such stem cells may constitute a source of specialized cell types for a wide range of therapeutic applications.

While the invention has been described with respect to certain specific embodiments, it will be appreciated that many modifications and changes thereof may be made by those skilled in the art without departing from the spirit of the invention. It is intended, therefore, by the appended claims to cover all modifications and changes that fall within the true spirit and scope of the invention.

What is claimed is:

1. A method for producing primate gynogenetic pluripotent cells comprising:
   (a) providing a primate oocyte in metaphase II;
   (b) activating said primate oocyte using activation conditions selected from the group consisting of: contacting the oocyte with a calcium ionophore, contacting the oocyte with a protein synthesis inhibitor, contacting the oocyte with phosphorylation inhibitor, and any combination thereof, to produce an activated oocyte,
   (c) culturing said activated oocyte to produce a gynogenetic blastocyst having an inner cell mass;
   (d) isolating said inner cell mass or isolated cells therefrom and transferring said inner cell mass or isolated cells therefrom into an in vitro culture that inhibits differentiation of said inner cell mass or isolated cells therefrom; and
   (e) culturing said inner cell mass or isolated cells therefrom or cells derived therefrom during inner cell mass proliferation in a culture that maintains the inner cell mass cells or cells therefrom in the undifferentiated state thereby producing a primate gynogenetic pluripotent stem cell.

2. The method of claim 1, wherein said calcium ionophore is A23187 or Ionomycin.

3. The method of claim 1, wherein said protein synthesis inhibitor is cycloheximide or puromycin.

4. The method of claim 1, wherein said phosphorylation inhibitor is 6-DMAP (dimethylaminopurine).

5. The method of claim 1, wherein the primate oocyte is human.

6. The method of claim 1, wherein said method further comprises a step of differentiating in vitro said undifferentiated primate gynogenetic pluripotent cells to produce primate gynogenetic differentiated cells.

7. The method of claim 1, wherein said primate oocyte is genetically modified.

8. The method of claim 3, wherein said protein synthesis inhibitor is puromycin.

* * * * *